US008129194B2

(12) United States Patent
Riviello

(10) Patent No.: US 8,129,194 B2
(45) Date of Patent: Mar. 6, 2012

(54) METHOD OF SIMULTANEOUS ANION AND CATION SUPPRESSION IN A CONTINUOUS ELECTRODEIONIZATION APPARATUS

(75) Inventor: John M. Riviello, Santa Cruz, CA (US)

(73) Assignee: Trovion Singapore Pte. Ltd., Co., Singapore (SG)

(*) Notice: Subject to any disclaimer, the term of this patent is extended or adjusted under 35 U.S.C. 154(b) by 0 days.

(21) Appl. No.: 12/930,758

(22) Filed: Jan. 14, 2011

(65) Prior Publication Data

US 2011/0114489 A1    May 19, 2011

Related U.S. Application Data

(62) Division of application No. 11/403,737, filed on Apr. 12, 2006, now Pat. No. 7,892,848.

(60) Provisional application No. 60/671,371, filed on Apr. 14, 2005.

(51) Int. Cl.
*G01N 30/26*    (2006.01)

(52) U.S. Cl. ..... 436/161; 73/61.55; 73/61.56; 73/61.58; 210/198.2; 210/656; 422/70

(58) Field of Classification Search .................. 436/161; 422/70; 210/656, 198.2; 73/61.52–61.58
See application file for complete search history.

(56) References Cited

U.S. PATENT DOCUMENTS

| 3,926,559 A | 12/1975 | Stevens ...................... 23/230 R |
| 4,687,561 A | 8/1987 | Kunz .......................... 204/182.5 |
| 5,045,204 A | 9/1991 | Dasgupta et al. ............. 210/635 |
| 5,248,426 A | 9/1993 | Stillian et al. ................. 210/635 |
| 5,352,360 A | 10/1994 | Stillian et al. ............... 210/198.2 |
| 5,518,622 A | 5/1996 | Stillian et al. ................. 210/635 |
| 5,569,365 A | 10/1996 | Rabin et al. .................... 204/450 |
| 5,597,481 A | 1/1997 | Stillian et al. ............... 210/198.2 |
| 5,633,171 A | 5/1997 | Small et al. ................... 436/161 |
| 5,759,405 A | 6/1998 | Anderson, Jr. et al. ....... 210/656 |
| 5,773,615 A | 6/1998 | Small et al. ................... 436/161 |
| 5,914,025 A | 6/1999 | Small ........................... 205/789 |
| 5,935,443 A | 8/1999 | Anderson, Jr. et al. ....... 210/656 |
| 6,027,643 A | 2/2000 | Small et al. ................. 210/198.2 |
| 6,077,434 A | 6/2000 | Srinivasan et al. ............ 210/635 |
| 6,200,477 B1 | 3/2001 | Anderson, Jr. et al. .... 210/198.2 |
| 6,235,197 B1 | 5/2001 | Anderson, Jr. et al. ....... 210/635 |

(Continued)

FOREIGN PATENT DOCUMENTS

EP    1048351 A2    11/2000

(Continued)

OTHER PUBLICATIONS

European Search Report of corresponding EP Application Serial No. 06740917.7, which corresponds with parent application (U.S. Appl. No. 11/403,737) to the present divisional application.

(Continued)

*Primary Examiner* — Jan Ludlow
(74) *Attorney, Agent, or Firm* — Shirley L. Church, Esq.

(57) ABSTRACT

The present invention pertains to a method of ion chromatography wherein a specialized electrodeionization (EDI) apparatus is used for simultaneous ion suppression of cations from a flowing base containing an anion sample of interest and ion suppression of anions from a flowing acid containing a cation sample of interest. The methods described herein allow for the ion suppression of samples containing chloride, nitrate, and other electrochemically active anions, as well as sodium, potassium, and other electrochemically active cations, without causing damage to the suppressor.

8 Claims, 20 Drawing Sheets

U.S. PATENT DOCUMENTS

| | | | |
|---|---|---|---|
| 6,284,124 B1 | 9/2001 | DiMascio et al. | 205/753 |
| 6,312,577 B1 | 11/2001 | Ganzi et al. | 204/524 |
| 6,325,976 B1 | 12/2001 | Small et al. | 422/70 |
| 6,328,885 B1 | 12/2001 | Srinivasan et al. | 210/198.2 |
| 6,468,804 B1 * | 10/2002 | Anderson et al. | 436/161 |
| 6,482,304 B1 | 11/2002 | Emery et al. | 204/524 |
| 6,495,371 B2 | 12/2002 | Small et al. | 436/161 |
| 6,508,985 B2 | 1/2003 | Small et al. | 422/70 |
| 6,558,551 B1 | 5/2003 | Anderson, Jr. et al. | 210/660 |
| 6,562,628 B1 | 5/2003 | Liu et al. | 436/161 |
| 6,596,145 B2 | 7/2003 | Moulin et al. | 204/634 |
| 6,610,546 B1 | 8/2003 | Liu et al. | 436/161 |
| 6,613,235 B1 | 9/2003 | Anderson, Jr. et al. | 210/670 |
| 6,649,037 B2 | 11/2003 | Liang et al. | 204/632 |
| 6,709,583 B2 | 3/2004 | Anderson, Jr. et al. | 210/198.2 |
| 6,808,608 B2 | 10/2004 | Srinivasan et al. | 204/533 |
| 6,824,662 B2 | 11/2004 | Liang et al. | 204/524 |
| 6,955,922 B1 | 10/2005 | Liu et al. | 436/174 |
| 2003/0127392 A1 | 7/2003 | Srinivasan et al. | 210/656 |
| 2004/0035802 A1 | 2/2004 | Emery et al. | 210/748 |

FOREIGN PATENT DOCUMENTS

| | | |
|---|---|---|
| WO | WO 02/04357 | 1/2002 |

OTHER PUBLICATIONS

Rabin, S. et al., "New Membrane-Based Electrolytic Suppressor Device for Suppressed Conductivity Detection in Ion Chromatography," *J. of Chromatog.*, 640 pp. 97-109 (1993).

* cited by examiner

Peak Identification

1. Fluoride
2. Acetate
3. Formate
4. Unknown
5. Chloride
6. Nitrate
7. Chlorate
8. Unknown
9. Carbonate
10. Unknown
11. Sulfate
12. Oxalate
13. Phosphate
14. Unknown

METHOD OF SIMULTANEOUS ANION AND CATION SUPPRESSION IN A CONTINUOUS ELECTRODEIONIZATION APPARATUS

RELATED APPLICATIONS

Benefit of priority under 35 U.S.C. §119(e) is claimed herein to U.S. Provisional Application No. 60/671,371, filed Apr. 14, 2005. The disclosure of the above referenced application is hereby incorporated by reference in its entirety herein. The parent application to the present divisional application, U.S. Ser. No. 11,403,737, titled "Method Of Ion Chromatography Wherein A Specialized Electrodeioniziation Apparatus Is Used", filed Apr. 12, 2006, is currently pending. A related application titled "Chambered Electrodeionization Apparatus With Uniform Current Density, And Method Of Use", U.S. Ser. No. 11/403,734, which was filed on the same day as the parent application to the present divisional application and is hereby incorporated by reference in its entirety, and has gone abandoned after publication as US 2006-0231403 A1 on Oct. 19, 2006.

BACKGROUND OF THE INVENTION

1. Field of the Invention

The present invention pertains to a method of ion chromatography wherein a specialized electrodeionization (EDI) apparatus is used.

2. Brief Description of the Background Art

This section describes background subject matter related to the disclosed embodiments of the present invention. There is no intention, either express or implied, that the background art discussed in this section legally constitutes prior art.

Ion chromatography (IC), a form of liquid chromatography, is a technique known in the art that is used for the analysis of anions and cations. IC of anions requires a different separation and detection chemistry than IC of cations.

As shown in FIG. 1, IC as typically known in the art, may include the following steps: (1) a chromatographic separation step, wherein an acid or base eluent is flowed through a chromatographic separation column to elute the ions contained within the column, (2) a suppression step, wherein the acid or base used for elution is suppressed and the ions eluted are enhanced, and (3) a detection step, wherein the eluted ions which have been enhanced are analyzed by way of an electrical conductivity detector.

In the chromatographic separation step of IC, ions of interest are typically eluted from a chromatographic separation column using an acid or base as the eluent. For the elution of anions a base is typically used and for the elution of cations an acid is typically used. It is desirable to use a relatively pure acid or base as the eluent, so that contaminant anions and cations are not introduced to the eluent. Thus, there is a need in the art for a convenient source of high purity acid and high purity base for use as an eluent in IC.

In the ion suppression step of IC, electrical conductivity of the acid or base eluent is suppressed, while the conductivity of the separated ions of interest are enhanced to aid in their detection. As is typical in the art for IC of anions, the base eluent will be suppressed (neutralized) in an anion suppressor and for IC of cations, the acid eluent will be suppressed (neutralized) in a cation suppressor. Techniques known in the art for ion suppression are described in detail in U.S. Pat. No. 3,926,559, which is hereby incorporated by reference.

The history of ion chromatography suppression as of 1993 was summarized in Rabin, S. et al., New Membrane-Based Electrolytic Suppressor Device for Suppressed Conductivity Detection in Ion Chromatography, J. of Chromatog. 640 (1993) 97-109, also incorporated herein by reference.

Many ion suppression methods described in the background art, for example U.S. Pat. No. 3,926,559, used a bed of ion exchange resin particles commonly referred to as a packed bed suppressor (PBS). The PBS requires periodic regeneration by flushing with an acid or base solution. While packed bed suppressors have proven useful in ion chromatography, there are a number of disadvantages of a PBS. These disadvantages include a) periodic regeneration of the PBS which interrupts sample analysis; b) a loss of resolution due to band broadening in the PBS over time; and c) changes in retention of certain analytes as a function of the degree of exhaustion of the PBS. To alleviate this problem, continuously regenerating electrolytic ion suppressors were introduced to the art. A few examples of these suppressors are listed below.

U.S. Pat. Nos. 5,248,426 and 5,352,360 to Stillian et al., issued Sep. 28, 1993 and Oct. 4, 1994, respectively describe a method and apparatus for a form of suppressor that uses a direct current power controller, which generates an electric field across two platinum electrodes to electrolyze water in regenerant channels of the apparatus. Functionalized ion-exchange screens are present in the regenerant chambers to facilitate electric current passage with the permselective ion-exchange membrane defining the chromatography eluent chamber.

U.S. Pat. Nos. 6,077,434 and 6,328,885 to Srinivasan et al., issued Jun. 20, 2000 and Dec. 11, 2001, respectively, describe a method and apparatus for increasing the current efficiency of suppressor and suppress-like pretreatment devices for the purpose of suppressing a high concentration of eluent.

U.S. Pat. Nos. 6,325,976; 6,495,371; and 6,508,985 to Small et al., issued Dec. 4, 2001, Dec. 17, 2002, and Jan. 21, 2003 respectively, describe an electrolytic suppressor, which includes a suppressor bed of ion exchange resin, an electrode chamber with electrodes in contact with the resin bed, and a recycle conduit between the suppressor outlet port and the electrode chamber, and a method for using such electrolytic suppressor.

U.S. Pat. No. 6,562,628 to Liu et al., issued May 13, 2003 describes a combination electrolytic suppressor and separate eluent generator and method. The suppressor includes a chromatography effluent flow channel, an ion receiving flow channel, and a first suppressor ion exchange barrier there between permeable to electrolyte ions but not liquid flow. Acid or base electrolytically generated in the first generator electrode chamber flows as an eluent stream to the chromatographic separator.

While electrolytic suppressors are the predominant suppressor in IC, there are draw backs to this type of suppressor. The eluent anion for use in cation analysis is drawn towards the anode. The oxidative nature of the anode electrochemistry limits the choice of eluents to non-electrochemically active anions such as sulfate or methane sulfonate. Common mineral acids such as hydrochloric acid or nitric acid cannot be used because at the anode, they are oxidized and the reaction products (such as hypochlorite) damage the anion exchange material. This results in increased resistance of the electrolytic suppressor, poor suppression capacity and ultimately failure of the suppressor.

In cation analysis, where a sample may contain large quantities of chloride, such as brine or seawater, the chloride from the sample is also removed from the suppressor and can cause a similar type of damage. Thus, there is a need in the art for a cation suppressor compatible with chloride, nitrate and other electrochemically active anions.

ABBREVIATIONS AND DEFINITIONS

The following terms and abbreviations are defined to provide the reader with a better understanding of the invention.
The following abbreviations are used herein:
CEDI=continuous electrodeionization;
EDI=electrodeionization;
IC=ion chromatography;
PBS=packed bed suppressor.

The terms "eluant" and "eluent" refer to the substance used to effect the separation of ions from a chromatographic separation column in an elution process. Example eluents may include, but are not limited to, an acid or a base.

The term "elution" refers to the chromatographic process of using an eluent to extract ions from a chromatographic separation column.

The term "eluate" refers to the product or substance that is separated out in an elution process.

DETAILED DESCRIPTION OF EXEMPLARY EMBODIMENTS OF THE INVENTION

As a preface to the detailed description presented below, it should be noted that, as used in this specification and the appended claims, the singular forms "a", "an", and "the" include plural referents, unless the context clearly dictates otherwise.

Use of the term "about" herein indicates that the named variable may vary to ±10%.

The present invention pertains to a method of ion chromatography wherein a specialized electrodeionization (EDI) apparatus is used for (1) the preparation of a pure acid or pure base for use as an eluent in a chromatographic separation column and/or (2) for ion suppression (or neutralization) of the acid or base after it has been used to elute ions from a chromatographic separation column.

Figure 1:
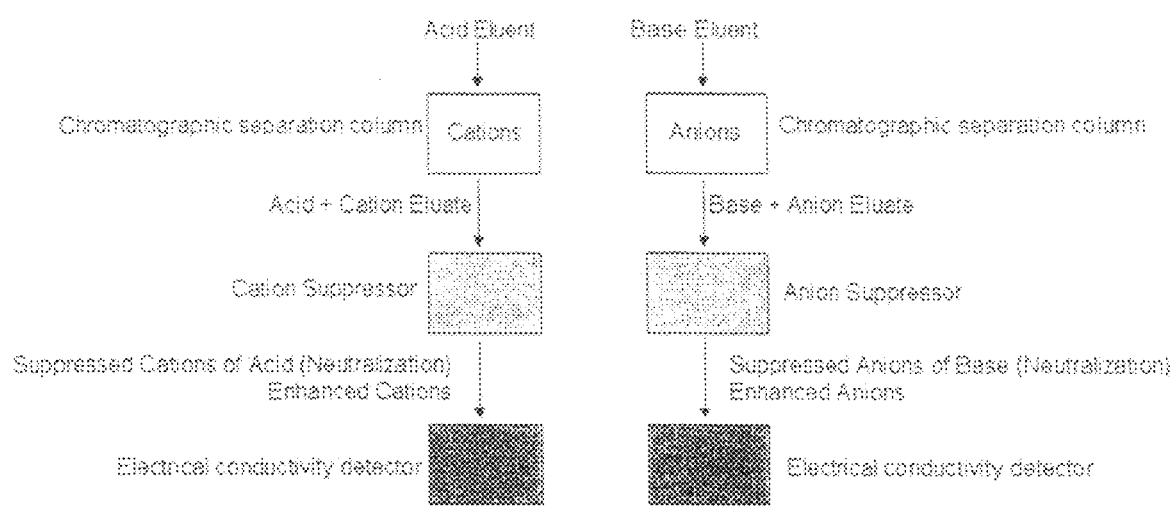
FIG. 1 depicts ion chromatography as typically known in the art, with the following steps: (1) a chromatographic separation step, wherein an acid or base eluent is flowed through a chromatographic separation column to elute the ions contained within the column, (2) a suppression step, wherein the acid or base used for elution is suppressed and the ions eluted are enhanced, and (3) a detection step, wherein the eluted ions which have been enhanced are analyzed by way of an electrical conductivity detector.
Figure 2:
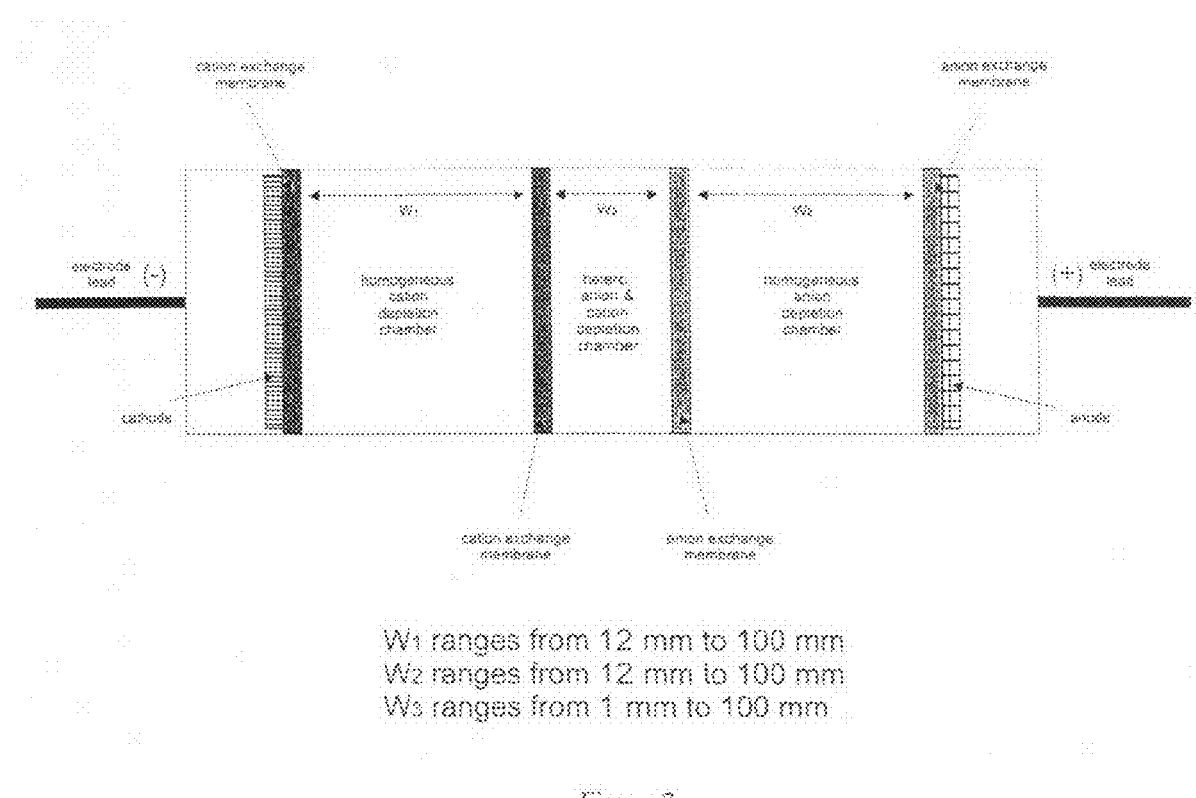
FIG. 2 shows a five chambered CEDI apparatus of the kind described in detail in the co-filed application entitled Chambered Electrodeionization Apparatus with Uniform Current Density, and Method of Use. This apparatus is used in one embodiment of the present invention. This EDI apparatus contains a cathode chamber, a homogeneous cation depletion chamber, a central heterogeneous anion and cation depletion chamber, a homogeneous anion depletion chamber, and an anode chamber. All of the five chambers are in electrical connection.

FIG. 2 shows a five chambered CEDI apparatus of the kind described in detail in the co-filed application entitled Chambered Electrodeionization Apparatus with Uniform Current Density, and Method of Use. The CEDI apparatus depicted in FIG. 2 is of the kind that may be used in the method for trace ion removal in the present invention. Thus, the method for the preparation of pure acids and bases for use in ion chromatography may use the CEDI apparatus depicted in FIG. 2.

The CEDI apparatus shown in FIG. 2 is an example of a CEDI apparatus, which consists of at least five discreet membrane bound chambers in electrical connection, comprising: (1) a cathode chamber; (2) at least one homogeneous cation depletion chamber; (3) a central heterogeneous anion and cation depletion chamber; (4) at least one homogeneous anion depletion chamber; and (5) an anode chamber. When additional (more than five) membrane bound chambers are present, they are typically present in pairs of additional homogeneous anion and cation depletion chambers, which are added in line next to existing like chambers, which are present between an electrode and the central heterogeneous anion and cation depletion chamber. An electrical current runs through the CEDI apparatus transverse to the membranes.

The cathode chamber shares a cation exchange membrane with a homogeneous cation depletion chamber, and contains a cathode that is in direct electrical contact with the cation exchange membrane.

Each homogeneous cation depletion chamber is bounded by two cation exchange membranes and contains a volume of homogeneous cation exchange material. The cation exchange material may include cation exchange resins, cation exchange particles, cation exchange fibers, cation exchange screens, cation exchange monoliths, and combinations thereof. Commonly, the cation exchange material is a volume of homogeneous cation exchange resin.

In a CEDI apparatus of the kind used to practice the present invention, each homogeneous cation depletion chamber exhibits a thickness ($w_1$) which may range from about 12 mm to about 100 mm. Typically, a homogeneous cation depletion chamber has a thickness ($w_1$) ranging from about 15 mm to about 40 mm.

The central heterogeneous anion and cation depletion chamber is bounded by a cation exchange membrane from a homogeneous cation depletion chamber and an anion exchange membrane from a homogeneous anion depletion chamber, and the chamber contains a heterogeneous mix of anion and cation ion exchange material. The ion exchange material is selected from the group consisting of ion exchange resins, ion exchange particles, ion exchange fibers, ion exchange screens, ion exchange monoliths, and combinations thereof. Typically, the ion exchange material is a heterogeneous mixed bed of resins comprising a mixture of cation exchange resins and anion exchange resins.

In a CEDI apparatus of the kind used to practice the present invention, a central heterogeneous anion and cation depletion chamber exhibits a thickness ($w_3$) which may range from about 1 mm to about 100 mm. Typically, the central heterogeneous anion and cation depletion chamber has a thickness ($w_3$) ranging from about 4.5 mm to about 12 mm.

Each homogeneous anion depletion chamber is bounded by two anion exchange membranes and contains a volume of homogeneous anion exchange material. The anion exchange material is selected from the group consisting of anion exchange resins, anion exchange particles, anion exchange fibers, anion exchange screens, anion exchange monoliths, and combinations thereof. Commonly, the anion exchange material is a volume of homogeneous anion exchange resin.

In a CEDI apparatus of the kind used to practice the present invention, each homogeneous anion depletion chamber thickness ($w_2$) which ranges from about 12 mm to about 100 mm. Typically, a homogeneous anion depletion chamber has a thickness ($w_2$) ranging from about 15 mm to about 40 mm.

Commonly, a CEDI apparatus used to practice the present invention has a ratio of the width of the summation of homogeneous cation depletion chamber(s) to the central heterogeneous anion and cation depletion chamber to the summation of homogeneous anion depletion chamber(s) ($w_1:w_3:w_2$) that ranges from about 1:1:1 to 20:1:20. In general, the width of the summation of homogeneous cation depletion chamber(s) ($w_1$) is equal to the width of the summation of homogeneous anion depletion chamber(s) ($w_2$), but in some specialized instances, it may be desirable to have one depletion chamber larger than the other.

The anode chamber shares an anion exchange membrane with a homogeneous anion depletion chamber, and contains an anode that is in direct electrical contact with the anion exchange membrane.

Figure 3:
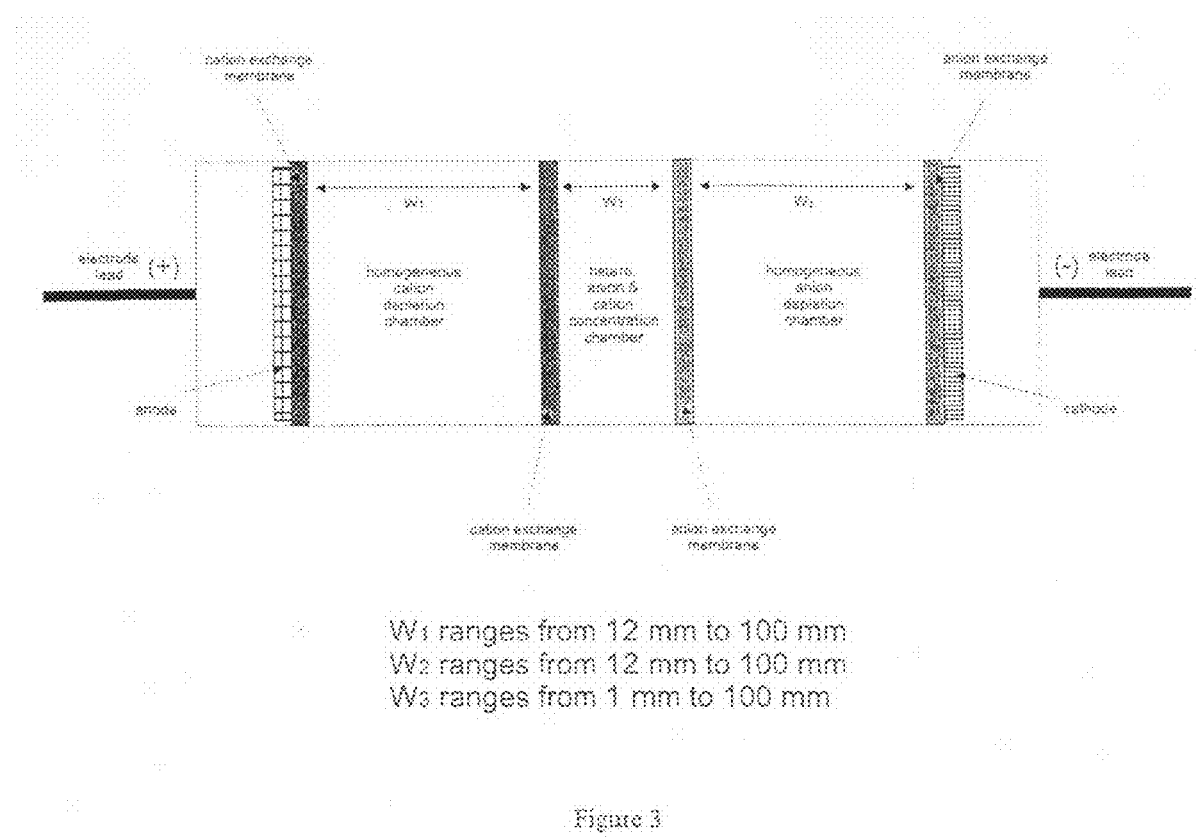
FIG. 3 shows the five chambered CEDI apparatus of the kind shown in FIG. 2, where the polarity has been reversed. This apparatus is used in another embodiment of the present invention. This EDI apparatus contains an anode chamber, a homogeneous cation depletion chamber, a central heterogeneous anion and cation concentration chamber, a homogeneous anion depletion chamber, and a cathode chamber. All of the five chambers are in electrical connection.

FIG. 3 shows the five chambered CEDI apparatus of the kind shown in FIG. 2, where the polarity has been reversed. This apparatus is of the kind used to practice several methods of the present invention. The CEDI apparatus depicted in FIG. 3 is of the kind that may be used in the method for ion suppression, and for acid and base neutralization as disclosed in the present invention. The method for the suppression of acids and bases by way of neutralization in ion chromatography may use the CEDI apparatus depicted in FIG. 3. Also, the method of simultaneous trace ion removal and ion suppression disclosed in the present invention uses the CEDI apparatus depicted in FIG. 3.

The CEDI apparatus shown in FIG. 3 is an example of a CEDI apparatus, which consists of at least five discreet membrane bound chambers in electrical connection, comprising: (1) an anode chamber; (2) at least one homogeneous cation depletion chamber; (3) a central heterogeneous anion and cation concentration chamber; (4) at least one homogeneous anion depletion chamber; and (5) a cathode chamber. When additional (more than five) membrane bound chambers are present, they are typically present in pairs of additional homogeneous anion and cation depletion chambers, which are added in line next to existing like chambers, which are present between an electrode and the central heterogeneous anion and cation concentration chamber. An electrical current runs through the CEDI apparatus transverse to the membranes.

The anode chamber shares a cation exchange membrane with a homogeneous cation depletion chamber, and contains an anode that is in direct electrical contact with the cation exchange membrane.

Each homogeneous cation depletion chamber is bounded by two cation exchange membranes and contains a volume of homogeneous cation exchange material. The cation exchange material may include cation exchange resins, cation exchange particles, cation exchange fibers, cation exchange screens, cation exchange monoliths, and combinations thereof. Commonly, the cation exchange material is a volume of homogeneous cation exchange resin.

In a CEDI apparatus of the kind used to practice the present invention, each homogeneous cation depletion chamber exhibits a thickness ($w_1$) which may range from about 12 mm to about 100 mm. Typically, a homogeneous cation depletion chamber has a thickness ($w_1$) ranging from about 15 mm to about 40 mm.

The central heterogeneous anion and cation concentration chamber is bounded by a cation exchange membrane from a homogeneous cation depletion chamber and an anion exchange membrane from a homogeneous anion depletion chamber, and the chamber contains a heterogeneous mix of anion and cation ion exchange material. The ion exchange material is selected from the group consisting of ion exchange resins, ion exchange particles, ion exchange fibers, ion exchange screens, ion exchange monoliths, and combinations thereof. Typically, the ion exchange material is a heterogeneous mixed bed of resins comprising a mixture of cation exchange resins and anion exchange resins.

In a CEDI apparatus of the kind used to practice the present invention, a central heterogeneous anion and cation concentration chamber exhibits a thickness ($w_3$) which may range from about 1 mm to about 100 mm. Typically, the central heterogeneous anion and cation concentration chamber has a thickness ($w_3$) ranging from about 4.5 mm to about 12 mm.

Each homogeneous anion depletion chamber is bounded by two anion exchange membranes and contains a volume of homogeneous anion exchange material. The anion exchange material is selected from the group consisting of anion exchange resins, anion exchange particles, anion exchange fibers, anion exchange screens, anion exchange monoliths, and combinations thereof. Commonly, the anion exchange material is a volume of homogeneous anion exchange resin.

In a CEDI apparatus of the kind used to practice the present invention, each homogeneous anion depletion chamber thickness ($w_2$) which ranges from about 12 mm to about 100 mm. Typically, a homogeneous anion depletion chamber has a thickness ($w_2$) ranging from about 15 mm to about 40 mm.

Commonly, a CEDI apparatus used to practice the present invention has a ratio of the width of the summation of homogeneous cation depletion chamber(s) to the central heterogeneous anion and cation concentration chamber to the summation of homogeneous anion depletion chamber(s) ($w_1:w_3:w_2$) that ranges from about 1:1:1 to 20:1:20. In general, the width of the summation of homogeneous cation depletion chamber(s) ($w_1$) is equal to the width of the summation of homogeneous anion depletion chamber(s) ($w_2$), but in some specialized instances, it may be desirable to have one depletion chamber larger than the other.

The cathode chamber shares an anion exchange membrane with a homogeneous anion depletion chamber, and contains a cathode that is in direct electrical contact with the anion exchange membrane.

The ion exchange membranes used in the CEDI apparatuses to practice the present invention work by passive transfer and not reactive chemistry. They contain functional sites, which allow for the exchange of ions. The transfer of ions through the ion exchange membrane is based upon the charge of the ion. They will readily admit small ions but resist the passage of bulk water, for example and not by way of limitation. Ion exchange membranes may be anion exchange membranes or cation exchange membranes, wherein they are selective to anions or cations respectively. An anion exchange membrane will transport anions through the membrane, but the membrane prevents the bulk flow of liquid from one side of the membrane to the other. A cation exchange membrane will transport cations through the membrane, but the membrane prevents the bulk flow of liquid from one side of the membrane to the other. A property common to both types of membranes is that they must be conductive so that ions may migrate through the ion exchange membrane towards their respective electrodes.

An example of an advantageous anion exchange membrane is a microporous copolymer of styrene and divinylbenzene that has been chloromethylated and then the pendant —$CH_2Cl$ groups that were introduced to the aromatic rings are then quaternized with a tertiary amine $R_1R_2R_3N$. This results in a membrane which is a strong base anion exchanger. In some cases, the anion exchange membrane may also contain a binder polymer. An example of an anion exchange membrane that could be used in the present invention is the AMI-7000S membrane (Membranes International, Glen Rock, N.J.). Other anion exchange membranes which provide a strong base anion exchanger may be used.

An example of an advantageous cation exchange membrane is a microporous copolymer of styrene and divinylbenzene that has undergone sulfonation, resulting in the monosubstitution of —$SO_3H$ groups on the aromatic rings of the copolymer. This results in a membrane which is a strong acid cation exchanger. In some cases, the cation exchange membrane may also contain a binder polymer. One example of a cation exchange membrane that could be used in the present invention is the CMI-7000S membrane (Membranes International, Glen Rock, N.J.). Other cation exchange membranes which provide a strong acid cation exchanger may be used.

The ion exchange resins used in the CEDI apparatuses of the kind used to practice the present invention contain functional sites, which allow for the exchange of ions. The interaction between ions and the ion exchange resins is based upon the charge of the ion. They will readily admit small ions and molecules but resist the intrusion of species of even a few hundred molecular weight. Ion exchange resins may be anion exchange resins or cation exchange resins, wherein they are selective to anions or cations respectively.

An example of an advantageous anion exchange resin is a microporous copolymer of styrene and divinylbenzene that has been chloromethylated and then the pendant —$CH2Cl$ groups that were introduced to the aromatic rings are then quaternized with a tertiary amine $R_1R_2R_3N$. This results in a resin which is a strong base anion exchanger. There are several commercially available resins of this type. One example of an anion exchange resin that could be used in the present invention is the Dowex 1×4 resin (Dow Chemical Company, Midland, Mich.), which contains 4% divinylbenzene and is in the form $Cl^-$. Other anion exchange resins which provide a strong base anion exchanger may be used.

An example of an advantageous cation exchange resin is a microporous copolymer of styrene and divinylbenzene that has undergone sulfonation, resulting in the monosubstitution of —$SO_3H$ groups on the aromatic rings of the copolymer. This results in a resin which is a strong acid cation exchanger. There are several commercially available membranes of this type. One example of a cation exchange membrane that could be used in the present invention is the Dowex 50W×4 resin (Dow Chemical Company, Midland, Mich.), which contains 4% divinylbenzene and is in the ionic form H. Other cation exchange resins which provide a strong acid cation exchanger may be used.

Method of Practicing the Invention

Figure 4:
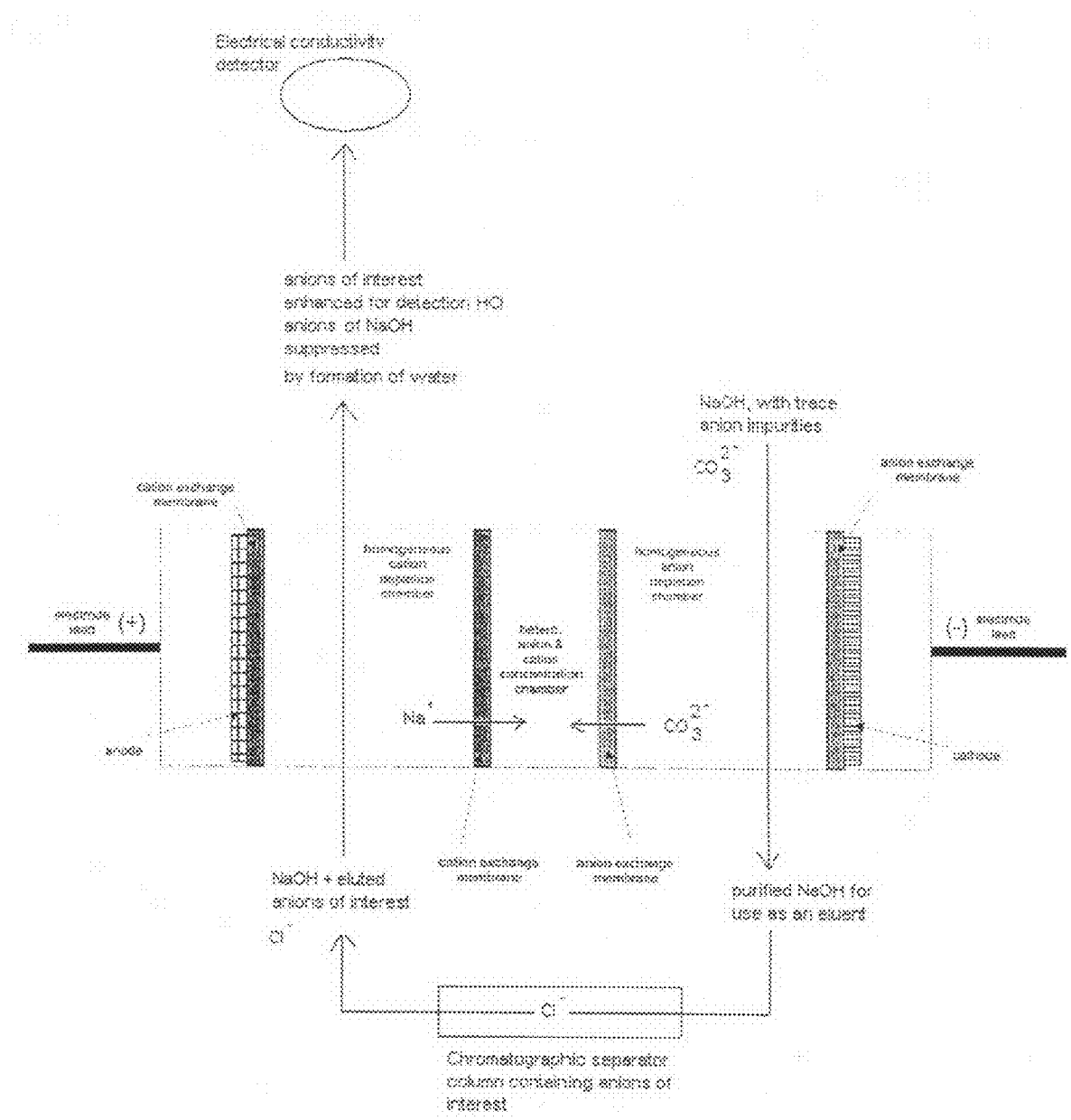
FIG. 4 shows a method of ion chromatography of anions by a method claimed in this invention. The purified base eluent used is generated in the CEDI apparatus of the kind shown in FIG. 3. The base containing the eluted anions is suppressed in the same CEDI apparatus.

Ion Chromatography:

FIG. 4 shows a method of ion chromatography of anions by a method claimed in this invention. The purified base eluent used is generated in the CEDI apparatus of the kind shown in FIG. 3. The base containing the eluted anions is suppressed in the same CEDI apparatus.

NaOH, containing trace anion impurities (such as $CO_3^{2-}$), is flowed through the homogeneous anion depletion chamber of the CEDI apparatus depicted in FIGS. 3 and 4, where the trace anions impurities (such as $CO_3^{2-}$) are removed by ion exchange and transferred to the heterogeneous anion and cation concentration chamber. Purified NaOH is flowed out of the homogeneous anion depletion chamber and is directed to a chromatographic separation column containing anions of interest (such as $Cl^-$). The anions of interest (such as $Cl^-$) are eluted from the chromatographic separation column by the purified NaOH. The NaOH containing the anions of interest (such as $Cl^-$) is then flowed from the chromatographic separation column back to the CEDI apparatus, but this time through the homogeneous cation depletion chamber. The anions of the NaOH are suppressed (neutralized to form water) and the anions of interest (such as $Cl^-$) are enhanced to their acid form (such as HCl) by way of ion exchange in the homogeneous cation depletion chamber. The enhanced anions (such as HCl), now in water instead of NaOH, are flowed out of the homogeneous cation depletion chamber and are directed to the electrical conductivity detector.

Figure 5:
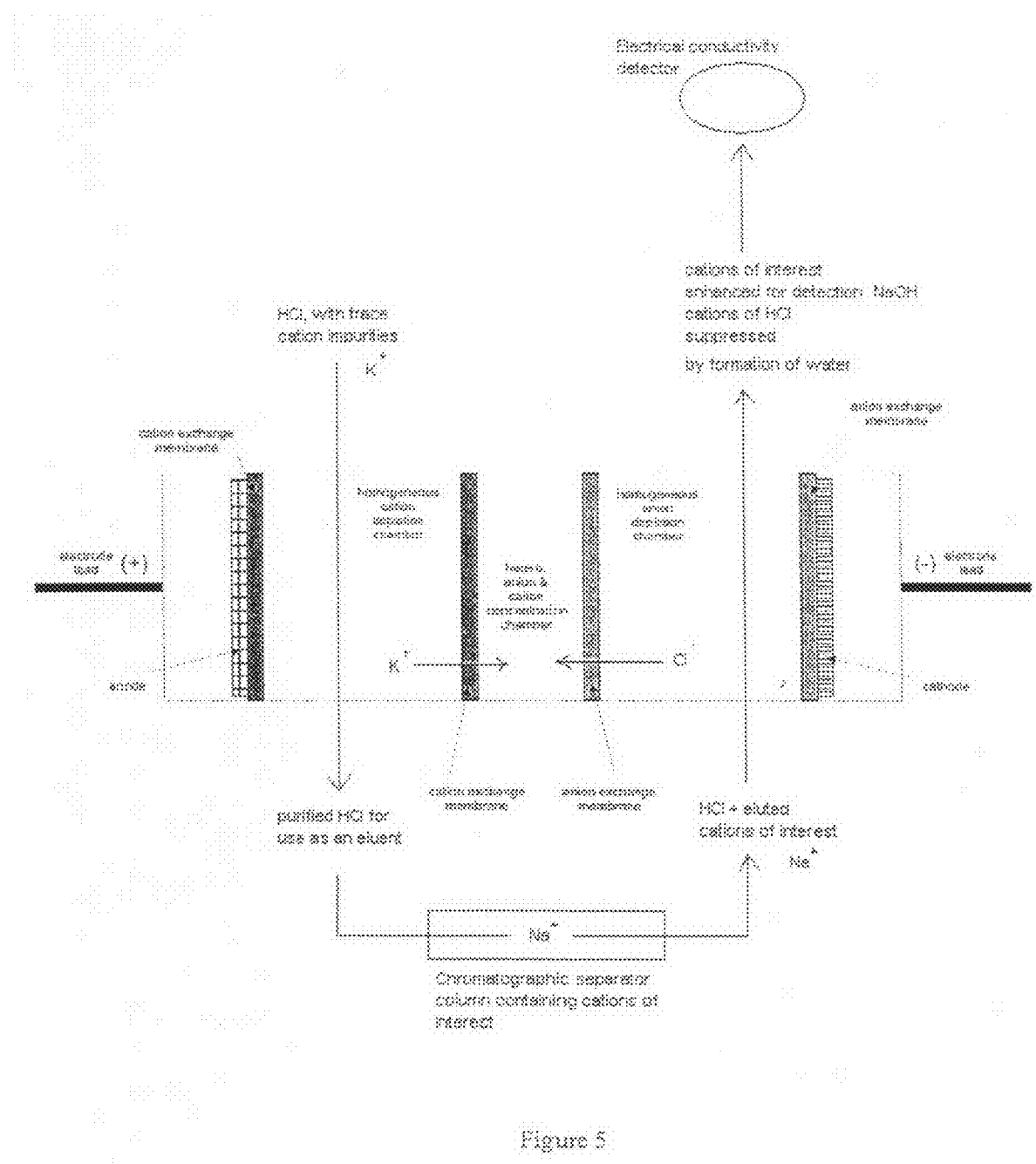
FIG. 5 shows a method of ion chromatography of cations by a method claimed in this invention. The purified acid eluent used is generated in the CEDI apparatus of the kind shown in FIG. 3. The acid containing the eluted cations is suppressed in the same CEDI apparatus.

FIG. 5 shows a method of ion chromatography of cations by a method claimed in this invention. The purified acid eluent used is generated in the CEDI apparatus of the kind shown in FIG. 3. The acid containing the eluted cations is suppressed in the same CEDI apparatus.

HCl, containing trace cation impurities (such as $K^+$), is flowed through the homogeneous cation depletion chamber of the CEDI apparatus depicted in FIGS. 3 and 5, where the trace cations impurities (such as $K^{+-}$) are removed by ion exchange and transferred to the heterogeneous anion and cation concentration chamber. Purified HCl is flowed out of the homogeneous cation depletion chamber and is directed to a chromatographic separation column containing cations of interest (such as $Na^+$). The cations of interest (such as $Na^+$) are eluted from the chromatographic separation column by the purified HCl. The HCl containing the cations of interest (such as $Na^+$) is then flowed from the chromatographic separation column back to the CEDI apparatus, but this time through the homogeneous anion depletion chamber. The cations of the HCl are suppressed (neutralized to form water) and the cations of interest (such as $Na^+$) are enhanced to their base form (such as NaOH) by way of ion exchange in the homogeneous anion depletion chamber. The enhanced cations (such as NaOH), now in water instead of HCl, are flowed out of the homogeneous cation depletion chamber and are directed to the electrical conductivity detector.

Purification of Acids and Bases by Trace Ion Removal:

One embodiment of the present invention is a method for the removal of trace ions using the CEDI apparatus described above in FIG. 2. This method includes the removal of trace cations in acids and trace anions in bases. After removal of trace anions and cations, these purified acids and bases can have several uses, such as eluents in ion chromatography.

Figure 6:
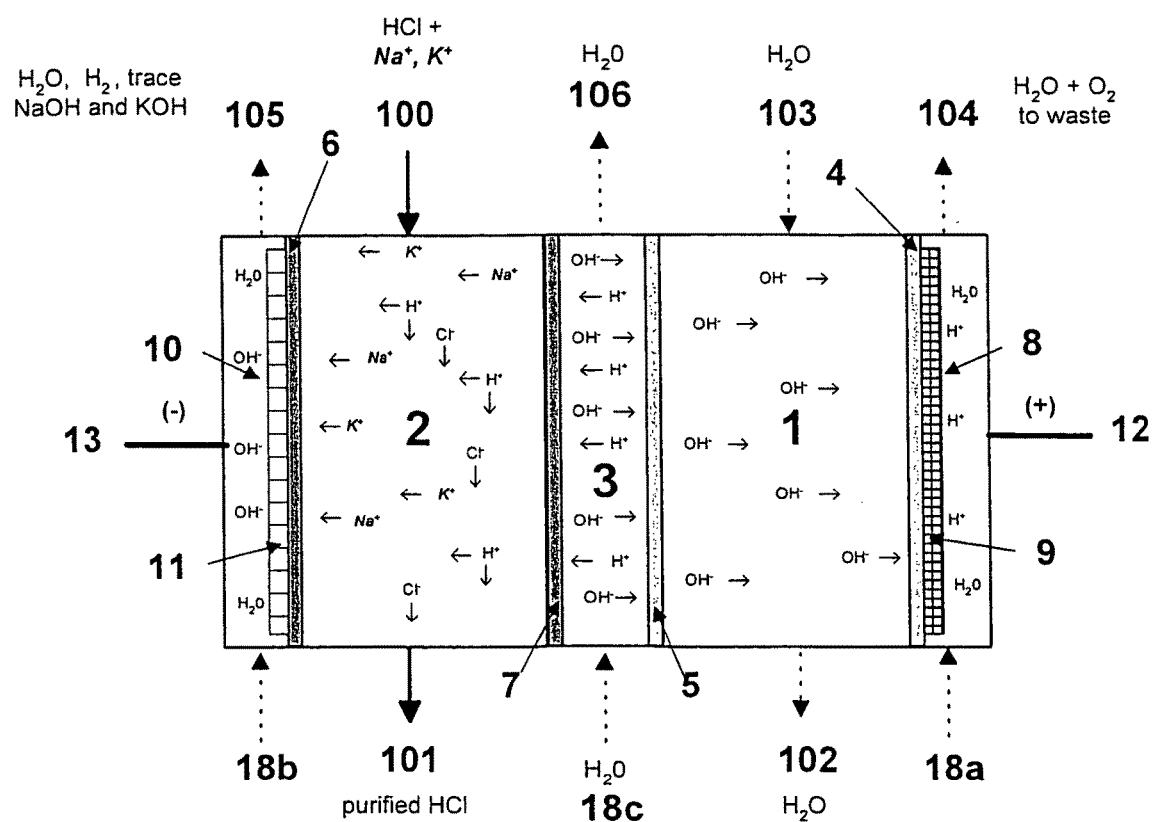
FIG. 6 shows the process fluid flow path for a method for trace cation removal from an acid using the apparatus shown in FIG. 2.

For example, as illustrated in FIG. 6, cationic impurities in hydrochloric acid are removed by passing the acid stream 100 through homogeneous cation depletion chamber 2. Trace cations such as sodium, potassium, ammonium, magnesium and calcium will be retained on the cation exchange material, and under the force of the applied electric field, the trace cations will electrophoretically migrate towards the cathode 11, through cation membrane 6, into cathode chamber 10 and will exit the cathode chamber in the base form (i.e. sodium hydroxide, potassium hydroxide) as cathode waste stream 105. The cation exchange material is continuously regenerated from the splitting of water in the central heterogeneous anion and cation depletion chamber 3 where hydronium ions are electrophoretically driven through cation membrane 7 towards cathode 11 in cathode chamber 10. The purified acid exits the homogeneous cation depletion chamber 2 as product stream 101.

During this process, there is a continuous flow of water from anode feed stream 18a, cathode feed stream 18b, and central heterogeneous anion and cation depletion chamber feed stream 18c. In the anode chamber 8, the water stream 18a provides water for electrolysis producing hydronium and oxygen gas, $O_2$ and anode waste stream 104. In the cathode chamber 10, the water stream 18b provides water for electrolysis producing hydroxide and hydrogen gas, $H_2$ and cathode waste stream 105. Any trace cations removed from acid sample stream 100 will exit in cathode waste stream 105. Water feed stream 103 flows through homogeneous anion depletion chamber 1 exiting as stream 102. The maximum concentration of acid that can be purified will depend primarily on the applied potential and the flow rate of the sample acid stream 100. For critical applications such as Inductively Coupled Plasma (ICP) or Inductively Coupled Plasma Mass Spectrometry (ICP-MS), the typical acid concentration is approximately 0.2 M and the flow rate is 0.5 mL/min-2 mL/min. The present invention will remove cations which may cause background interferences in ICP or ICP-MS.

Figure 7:
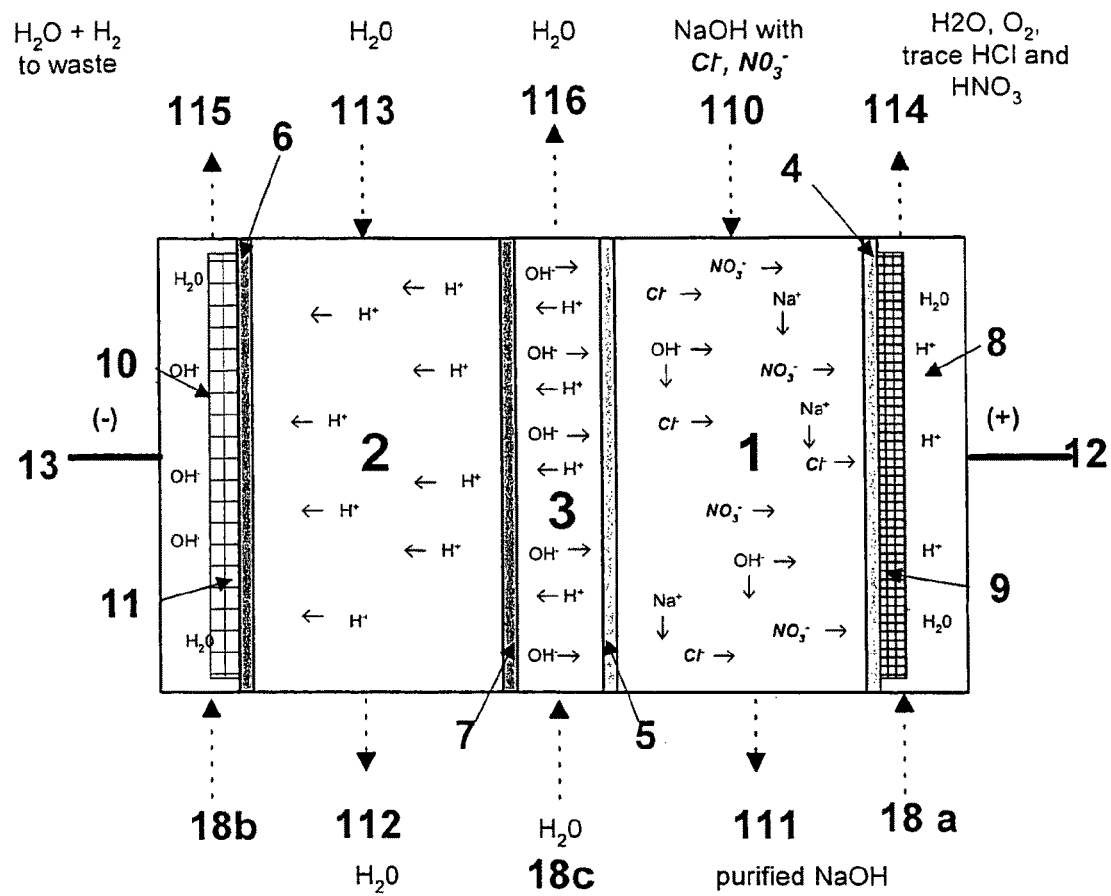
FIG. 7 shows the process fluid flow path for a method for trace anion removal from a base using the apparatus shown in FIG. 2.

Similarly, bases can be purified of trace anions as shown in FIG. 7. Trace anionic impurities such as chloride, sulfate, carbonate or nitrate can be removed from dilute bases such as sodium or potassium hydroxide. The sample base stream 110 is passed through homogeneous anion depletion chamber 1 where trace anions will be retained on the anion exchange material, and under the force of the applied electric field, the trace anions will electrophoretically migrate towards anode 9, through anion membrane 4, into anode chamber 8. The trace anions will exit the anode chamber 8 in the acid form (i.e. hydrochloric acid, sulfuric acid, carbonic acid) as anode waste stream 114. The anion exchange material is continuously regenerated from the splitting of water in central heterogeneous anion and cation depletion chamber 3 where hydroxide ions are electrophoretically driven through anion membrane 5 towards anode 9 in anode chamber 8. The purified base exits the homogeneous anion depletion chamber 1 as product stream 111.

During this process, there is a continuous flow of water from anode feed stream 18a, cathode feed stream 18b, and central chamber feed stream 18c. In the anode chamber 8, the water stream 18a provides water for electrolysis producing hydronium and oxygen gas, $O_2$ and anode waste stream 114. In the cathode chamber 10, the water stream 18b provides water for electrolysis producing hydroxide and hydrogen gas, $H_2$ and cathode waste stream 115. Any trace anions removed from base sample stream 110 will exit in anode waste stream 114. Water feed stream 113 flows through homogeneous cation depletion chamber 2 exiting as stream 112. The maximum concentration of base that can be purified will depend primarily on the applied potential and the flow rate of the base stream 110. For applications such as ion chromatography, the typical base concentration is approximately 0.01 M to 0.2 M and the flow rate is 0.2 mL/min-2 mL/min. The present invention will remove trace anions which can cause background interferences, increased noise and spurious peaks in ion chromatography.

Figure 8:
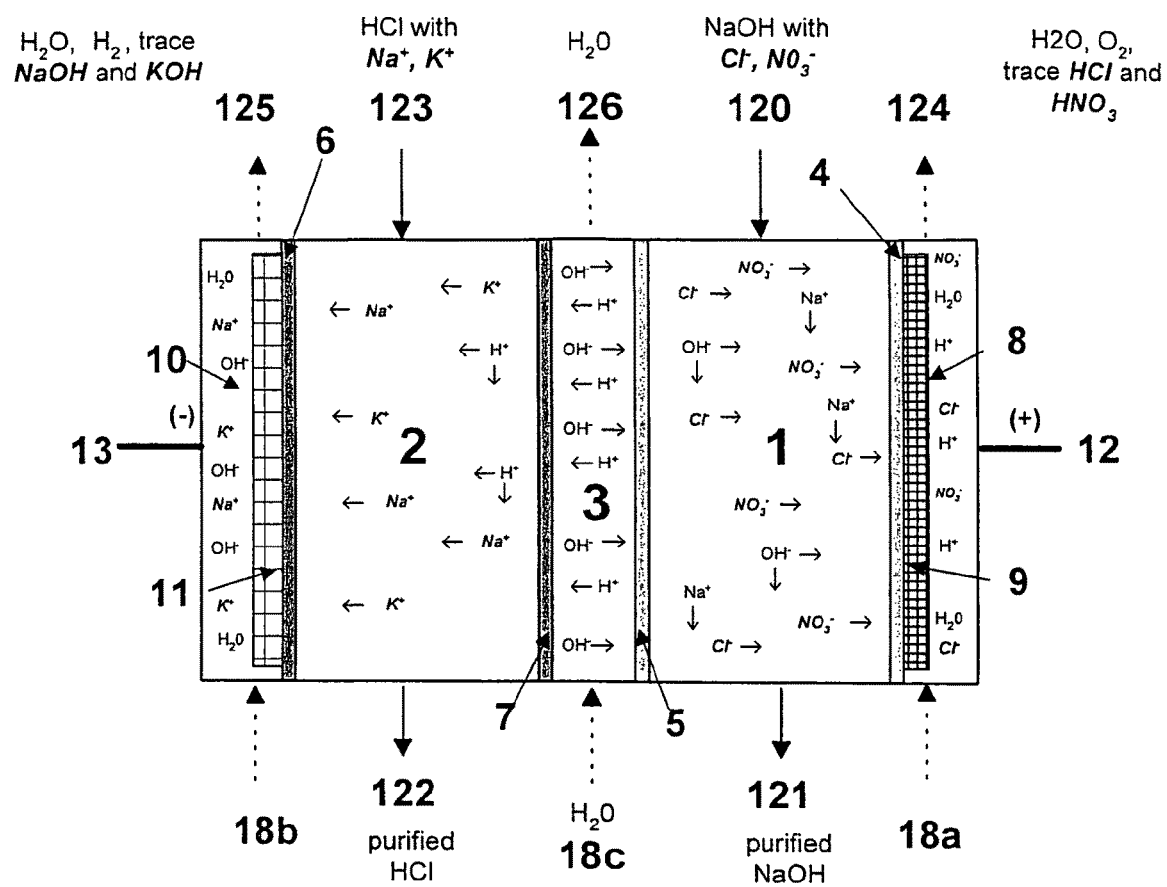
FIG. 8 shows the process fluid flow path for a method for simultaneous trace cation and trace anion removal from an acid and a base using the apparatus shown in FIG. 2.

As shown in FIG. 8, it is also possible to use the device for the simultaneous purification of an acid and a base. The process in FIG. 8 is identical to that of FIGS. 6 and 7. This configuration has the advantage of being able to purify electroactive acids such has hydrochloric acid or nitric acid since there is no direct contact of the acid with the electrodes, particularly the anode. Also, the electrolysis by-products, hydrogen gas and oxygen gas are produced in the cathode chamber 10 and anode chamber 8, respectively, thereby eliminating the complication of dissolved gases in the sample streams. Since a single power supply is used with the device in FIG. 7, it is important that the power supply be operated to accommodate the purification of the acid or base stream requiring the highest voltage or current.

Acid and Base Neutralization:

Another embodiment of the present invention is a method for acid and base neutralization using the CEDI apparatus described above in FIG. 3. This method is described below, as is shown in FIGS. 9 through 11.

Figure 9:
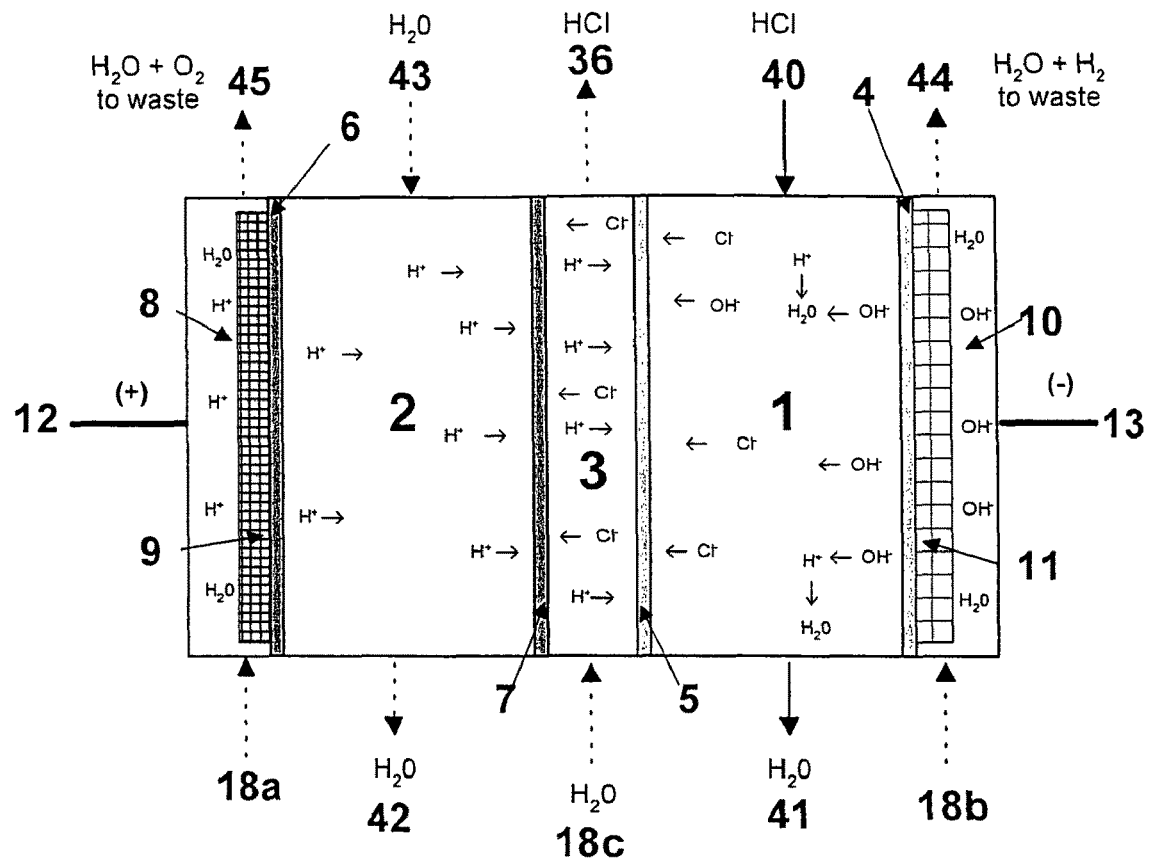
FIG. 9 shows the process fluid flow path for a method for acid neutralization using the apparatus shown in FIG. 3.

For example, in FIG. 9, a stream of hydrochloric acid 40 is pumped into homogeneous anion depletion chamber 1 in which the anion exchange material is in the hydroxide form and continually being regenerated from cathode 11 in cathode chamber 10. As the hydrochloric acid 40 passes through ion depletion chamber 1, chloride is retained on the anion exchange material and exchanged for hydroxide which combines with hydronium from the hydrochloric acid. The resulting product stream is water 41. The chloride ion in homogeneous anion depletion chamber 1 is electrophoretically driven towards the central heterogeneous anion and cation concentration chamber 3 under force of the anode 9 in anode chamber 8. As the chloride passes through anion membrane 5, hydronium is being electrophoretically driven from the anode chamber 8 through cation membrane 6, into ion depletion chamber 2, through cation membrane 7 and into the central heterogeneous anion and cation concentration chamber 3. The hydronium combines with the chloride forming hydrochloric acid which passes out of the central chamber 3 as waste stream 36.

Anode feed stream 18a flows into anode chamber 8 producing anode concentrate 45. Cathode feed stream 18b flows into cathode chamber 10 producing cathode concentrate 44. Feed stream 18c flows into the central heterogeneous anion and cation concentration chamber 3. Product stream 41 will be free of all anions, but may still contain cations, for example sodium, potassium or magnesium. These cations will exit homogeneous cation depletion chamber 2 in the hydroxide forms. If it is desirable to remove the cations, product stream 41 may be diverted to homogeneous cation depletion chamber 2 via inlet 43. In homogeneous cation depletion chamber 2, cations such as sodium, potassium and magnesium will be replaced with hydronium and the product stream 42 will be free of both anions and cations resulting in deionized water. (No figure included for this application). During this process, there is a continuous flow of water from anode feed stream 18a, cathode feed stream 18b, and central chamber feed stream 18c.

Figure 10:
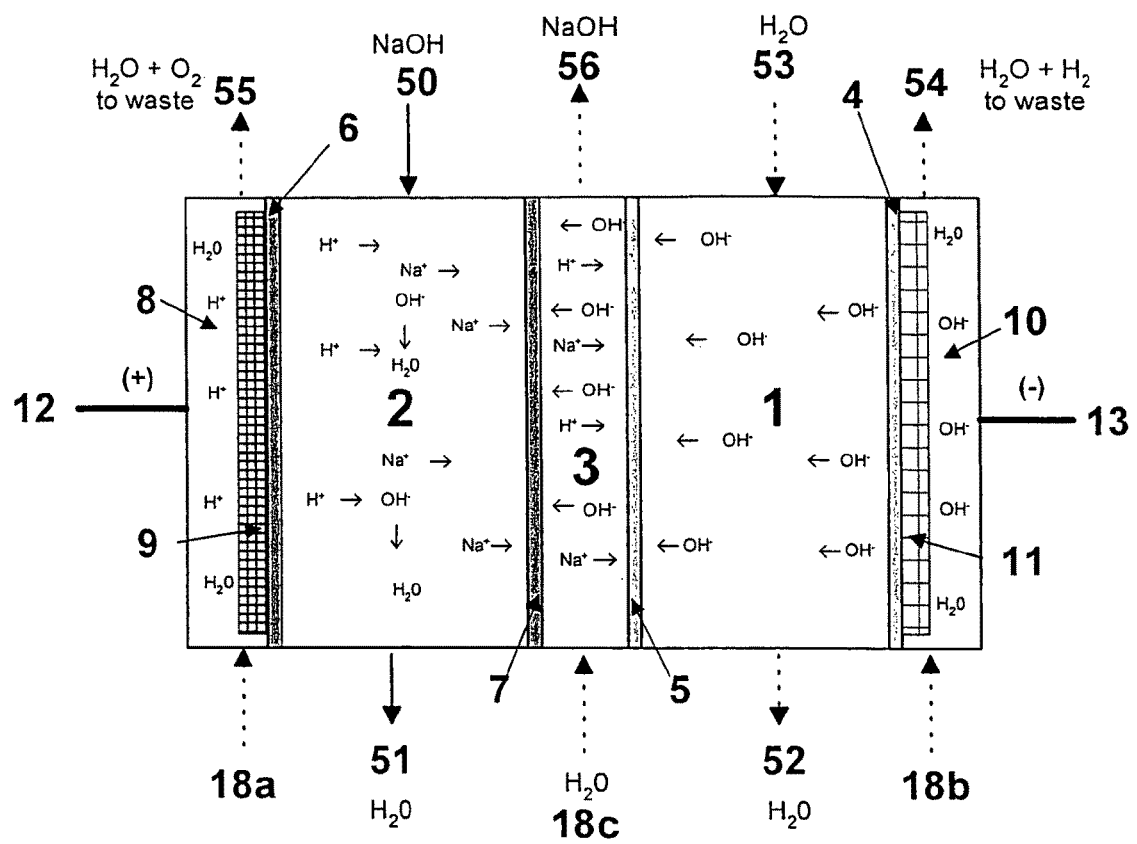
FIG. 10 shows the process fluid flow path for a method for base neutralization using the apparatus shown in FIG. 3.
Figure 11:
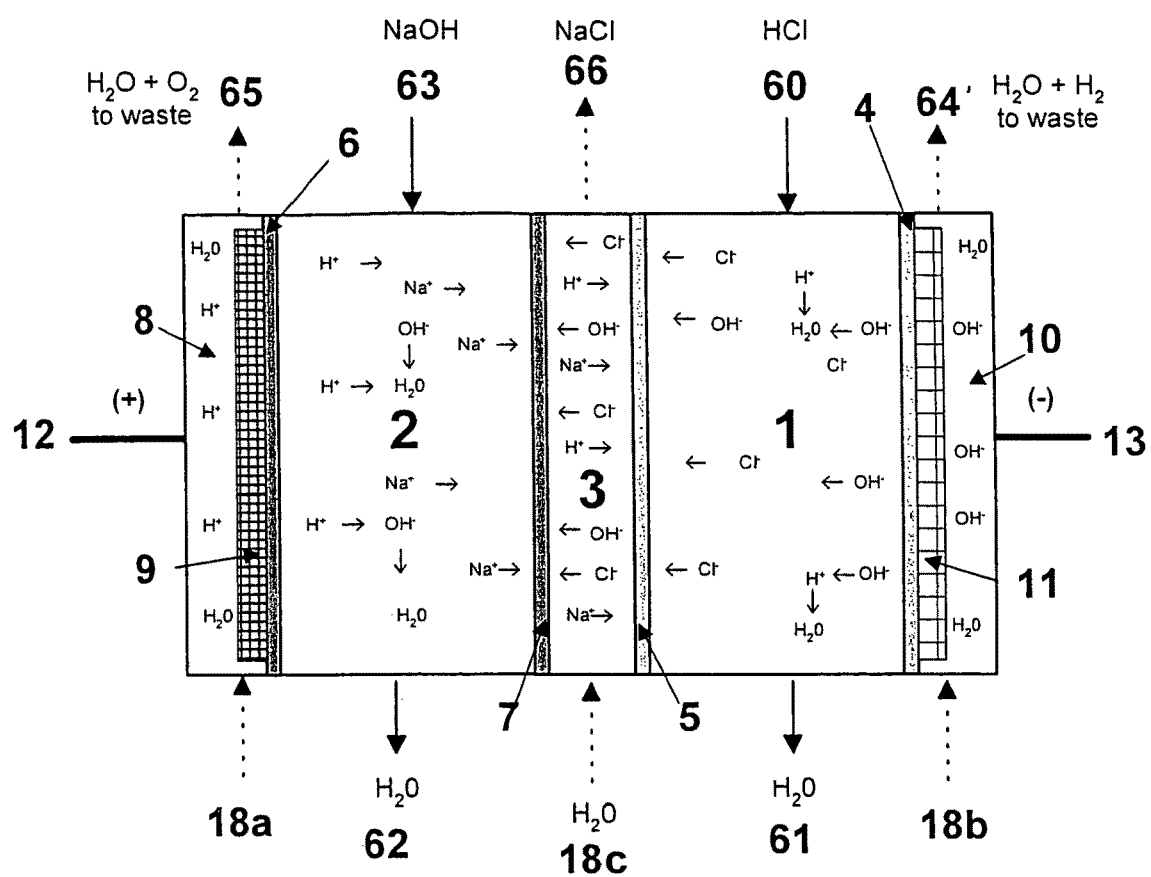
FIG. 11 shows the process fluid flow path for a method for simultaneous acid and base neutralization using the apparatus shown in FIG. 3.

The neutralization of base is shown in FIG. 10. For example, a stream of sodium hydroxide 50 is pumped into homogeneous cation depletion chamber 2 where the cation exchange material is in the hydronium form and continually being regenerated from anode 9 in anode chamber 8. As the sodium hydroxide 50 passes through homogeneous cation depletion chamber 2, sodium is retained on the cation exchange material and exchanged for hydronium which combines with hydroxide from the sodium hydroxide. The resulting product stream 51 is water. The sodium ion in homogeneous cation depletion chamber 2 is electrophoretically driven towards the central heterogeneous anion and cation concentration chamber 3 under force of the cathode 11 in cathode chamber 10. As the sodium passes through cation membrane 7, hydroxide is being electrophoretically driven from the cathode chamber 10 through anion membrane 4, into homogeneous anion depletion chamber 1, through anion membrane 5 and into the central chamber 3. The sodium combines with hydroxide forming sodium hydroxide which passes out of the central chamber 3 as waste stream 56.

Anode feed stream 18a and cathode feed stream 18b flow into the anode chamber 8 and cathode chamber 10, respectively, producing anode concentrate 55 and cathode concentrate 54, respectively. Product stream 51 will be free of all cations, but may still contain anions, for example chloride and sulfate. These anions will exit homogeneous anion depletion chamber 1 in their acid forms. If it is desirable to remove the anions, product stream 51 may be diverted to homogeneous anion depletion chamber 1 via inlet 53. In homogeneous anion depletion chamber 1, anions such as chloride and sulfate will be replaced with hydroxide and the product stream 52 will be free of both anions and cations resulting in deionized water. (Not shown in FIG. 10). During this process, there is a continuous flow of water from anode feed stream 18a, cathode feed stream 18b, and central heterogeneous anion and cation concentration chamber feed stream 18c.

The device can also be used for the simultaneous neutralization of an acid and base stream as shown in FIG. 11. The mechanism is identical as described in FIGS. 9 and 10, with the exception that the waste stream 66 from the central homogeneous anion and cation concentration chamber now contains the neutralization products (water and salt) from the acid and base feed streams. The applied voltage and current must be sufficient to allow complete neutralization of the acid or base of highest concentration.

As described with respect to FIG. 9, any cation present in the acid will exit ion depletion chamber 1 in the base form in water. Thus, it is possible to use this device to neutralize an acid sample prior to measuring the cation(s) concentration(s) by some analytical technique such as atomic absorption spectrometry, inductively coupled plasma (ICP), emission spectroscopy, inductively coupled plasma mass spectrometry (ICP-MS), ion chromatography (IC) or ion selective electrodes (ISE). The analytical measurement techniques suffer from interferences if the acid concentration of the sample is too high. By complete or partial neutralization of the sample prior to analysis, the acid matrix interference can be reduced. Depending on which analytical technique is being used, it may be desirable to have the product stream 41 (FIG. 9) or 61 (FIG. 11) connected directly to the analytical instrument of choice.

Similarly, as shown in FIG. 10, the CEDI apparatus can be used to neutralize base prior to measuring the anion concentration by some analytical technique such as flow injection analysis, ion chromatography or ion selective electrodes. These techniques suffer from matrix interferences if the base concentration of the sample is too high. By complete or partial neutralization of the sample prior to analysis, the base matrix interference can be reduced. Depending on which analytical technique is being used, it may be desirable to have the product stream 51 (FIG. 10) or 62 (FIG. 11) connected directly to the analytical instrument of choice.

The method disclosed here of using a specialized CEDI apparatus for acid and base neutralization gives an unexpected result. Although the neutralization of an acid or a base by ion exchange is a form of deionization, the background art teaches that EDI apparatuses are typically used for water purification, and the water stream, that is feeding into the EDI apparatus, should not be a strong acid or base (for example, see U.S. Pat. No. 6,808,608 column 11, lines 37-38).

Figure 13:
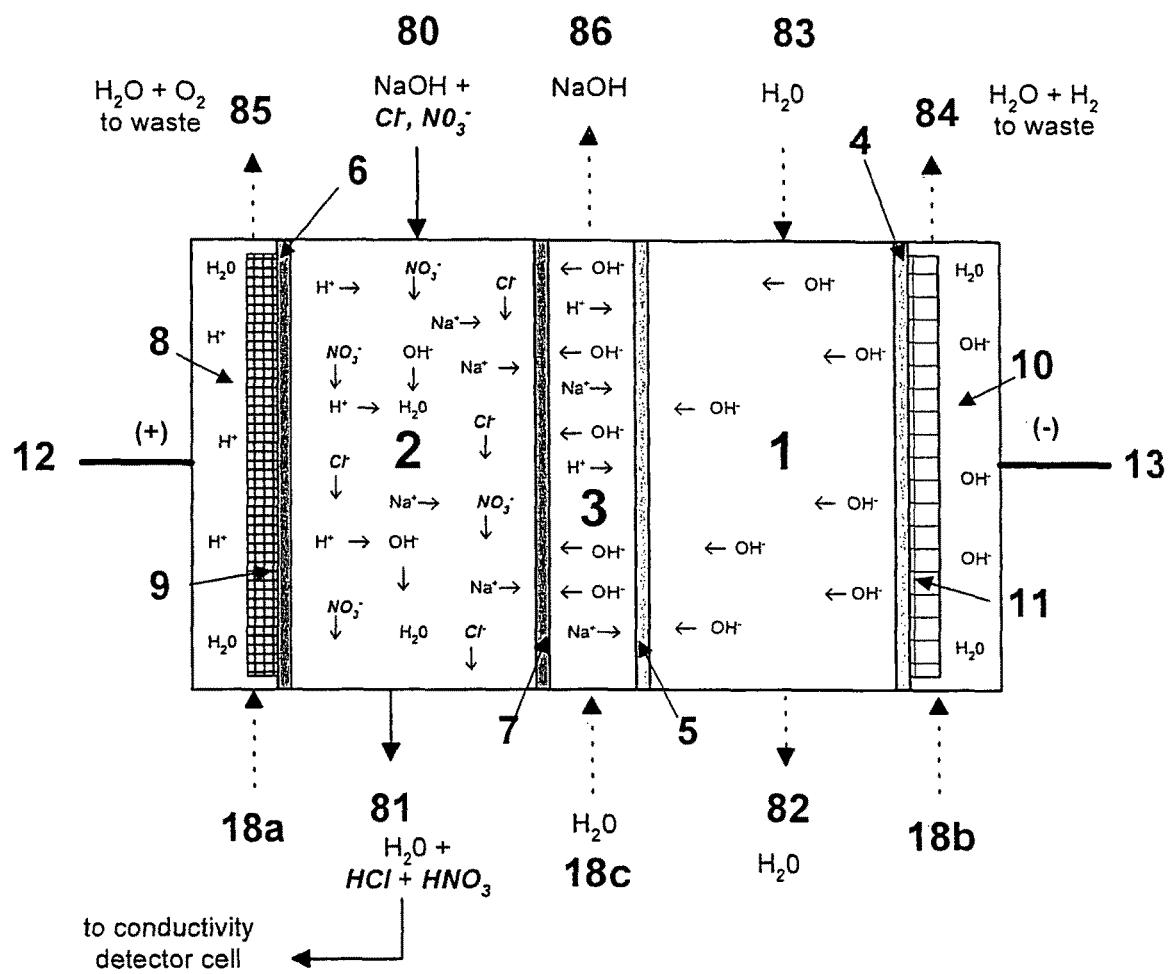
FIG. 13 shows the process fluid flow path for a method for anion suppression using the apparatus shown in FIG. 3.
Figure 14:
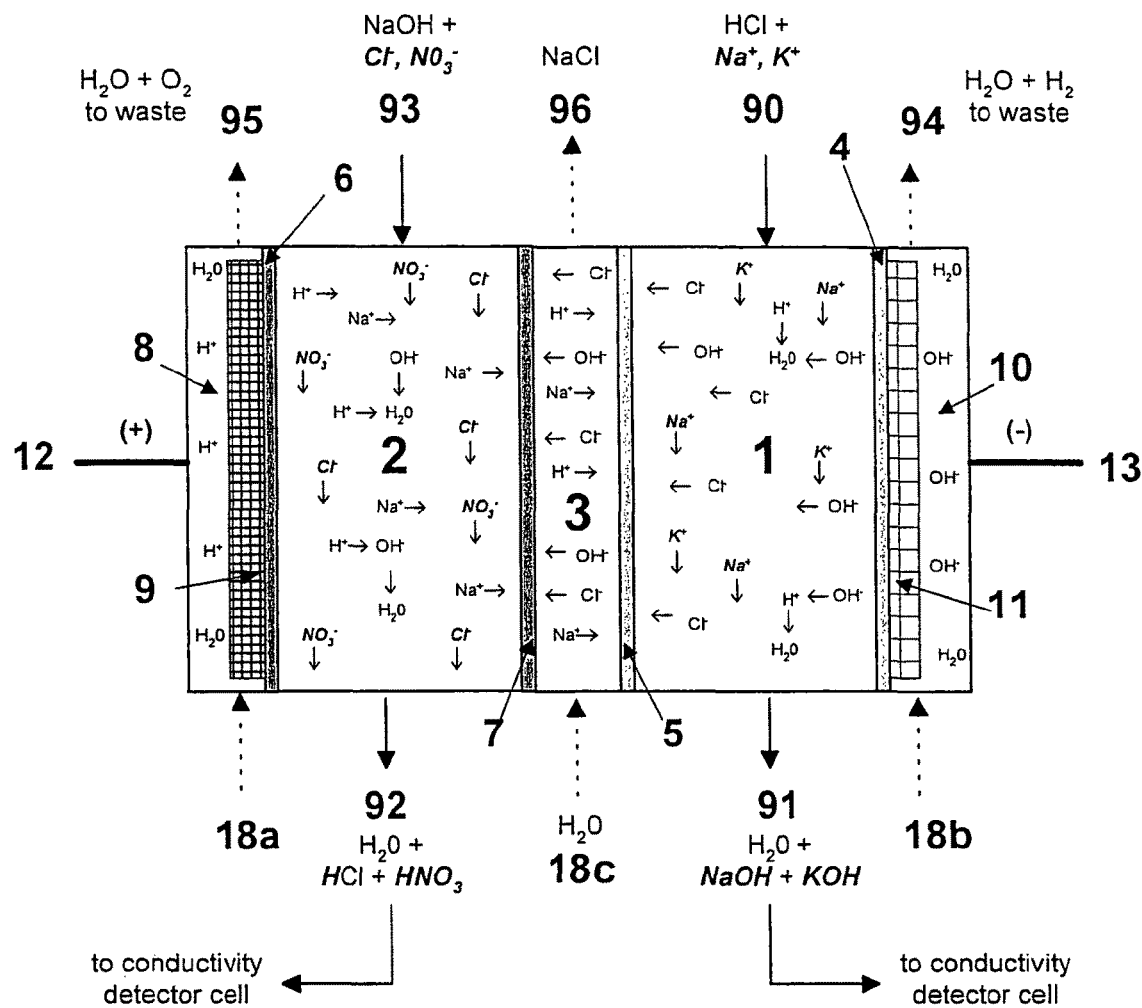
FIG. 14 shows the process fluid flow path for a method for simultaneous anion and cation suppression using the apparatus shown in FIG. 3.

Ion Suppression:

Another embodiment of the present invention is a method for ion suppression using the CEDI apparatus described above in FIG. 3. This method is described below, as is shown in FIGS. 12 through 14.

Figure 12:
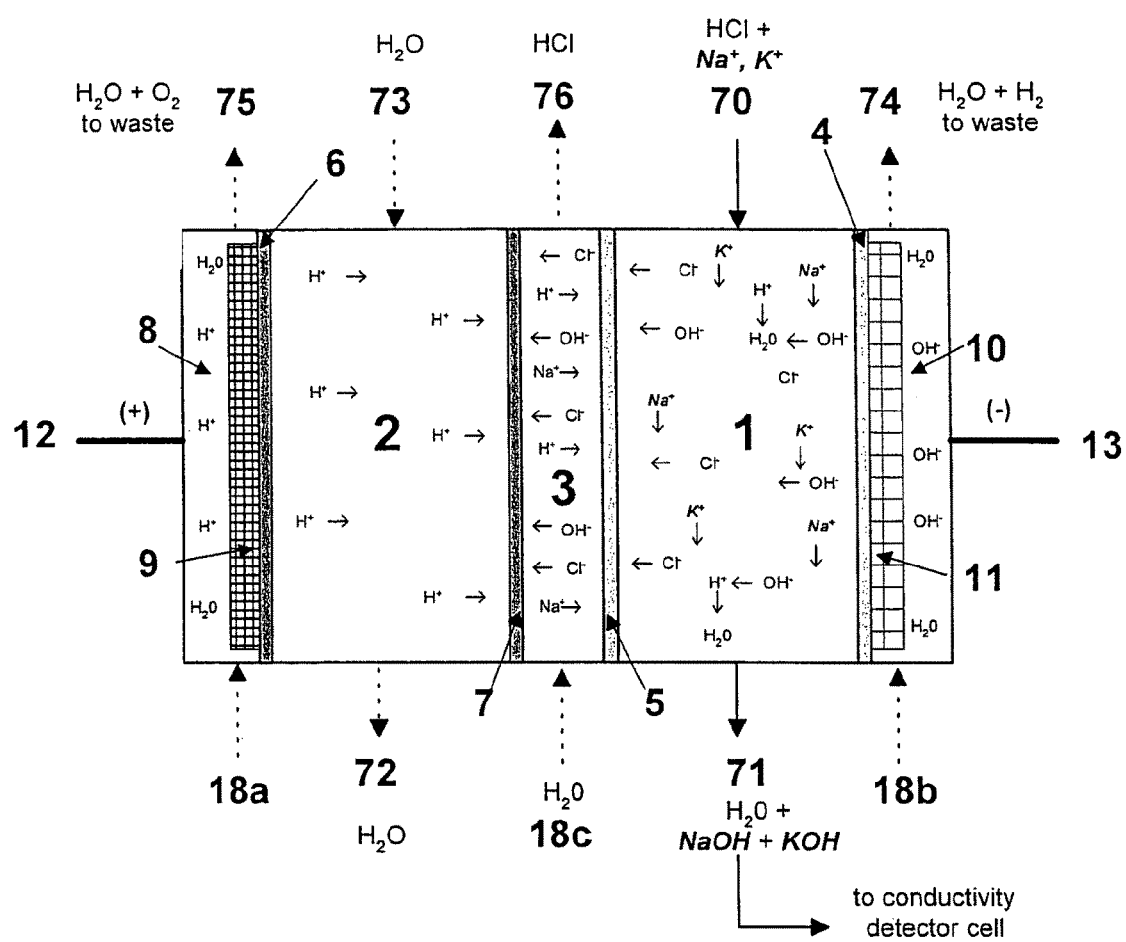
FIG. 12 shows the process fluid flow path for a method for cation suppression using the apparatus shown in FIG. 3.

FIG. 12 is an example showing the method of using the CEDI apparatus as a cation suppressor. In this application, an acid eluent such as hydrochloric, methanesulfonic or sulfuric acid is used for the separation of cations, primarily alkali and alkaline-earth metals as well ammonia and amines. Detection is accomplished by conductivity detection and the suppressor serves to reduce the conductance of the eluent (background conductivity) while increasing the conductive form of the cations by converting them to the hydroxide form.

The acid eluent (hydrochloric acid in this example) stream 70 from the cation separator (not shown) flows through homogeneous anion depletion chamber 1 in which the anion exchange material is in the hydroxide form and continually being regenerated from cathode 11 in cathode chamber 10. As the hydrochloric acid eluent 70 passes through homogeneous anion depletion chamber 1, chloride is retained on the anion exchange material and exchanged for hydroxide which combines with hydronium from the hydrochloric acid forming water which exits as product (eluent) stream 71.

The chloride in homogeneous anion depletion chamber 1 is electrophoretically driven towards the central heterogeneous anion and cation concentration chamber 3 under force of the anode 9 in anode chamber 8. As the chloride passes through anion membrane 5, hydronium is being electrophoretically driven from the anode chamber 8 through cation membrane 6, into homogeneous cation depletion chamber 2, through cation membrane 7 and into the central homogeneous anion and cation concentration chamber 3 where the hydronium combines with the chloride forming hydrochloric acid. The hydrochloric acid passes out of the central heterogeneous anion and cation concentration chamber 3 as waste stream 76.

Sample cations such as sodium, potassium, ammonium, calcium and magnesium present in product stream 71 will exit the homogeneous anion depletion chamber 1 as the corresponding base i.e. sodium hydroxide, potassium hydroxide, ammonium hydroxide, calcium hydroxide and magnesium hydroxide. The product stream 71 flows directly to the conductivity detector cell. During this process, there is a continuous flow of water from anode feed stream 18a, cathode feed stream 18b, and central chamber feed stream 18c. In the anode chamber 8, the water stream 18a provides water for electrolysis producing hydronium and oxygen gas, $O_2$ and anode waste stream 75. In the cathode chamber 10 the water stream 18b provides water for electrolysis producing hydroxide and hydrogen gas, $H_2$ and waste stream 74.

Compared to conventional electrochemical suppressors for ion chromatography, the embodiment in FIG. 12 offers the advantage of being compatible with electrochemically compatible eluents such as hydrochloric or nitric acids. In conventional electrochemical suppressors, the chloride or nitrate can be electrochemically oxidized at the anode and the oxidation products can irreversibly damage the ion exchange material used in the suppressor. In the method of the present invention, the anion (chloride or nitrate) is never in contact with the anode or cathode, thus eliminating the formation of electrochemically active products which can damage the ion exchange materials present in the device.

FIG. 13 is an example showing a method of the present invention for the suppression of anions in ion chromatography. In this application, an eluent containing either sodium hydroxide, potassium hydroxide, sodium carbonate or sodium bicarbonate is used for the separation of anions such as fluoride, chloride, sulfate, nitrate, phosphate as well as and organic acids. Detection is accomplished by conductivity and the suppressor serves to reduce the conductance of the eluent (background conductivity) while increasing the conductivity form of the anions of interested by detecting them as the hydronium or "acid" form.

The basic eluent (sodium hydroxide in this example) stream 80 from the anion separator (not shown) flows through homogeneous cation depletion chamber 2 in which the cation exchange material is in the hydronium form and continually being regenerated from anode 9 in anode chamber 8. As the sodium hydroxide eluent 80 passes through homogeneous cation depletion chamber 2, sodium is retained on the cation exchange material and exchanged for hydronium which combines with hydroxide from the sodium hydroxide forming water which exits as product (eluent) stream 81. The sodium in homogeneous cation depletion chamber 2 is electrophoretically driven towards the central heterogeneous anion and cation concentration chamber 3 under force of the cathode 11 in cathode chamber 10. As the sodium passes through cation membrane 7, hydroxide is being electrophoretically driven from the cathode chamber 10 through anion membrane 4, into homogeneous anion depletion chamber 1, through anion membrane 5 and into the central heterogeneous anion and cation concentration chamber 3 where the hydroxide combines with the sodium forming sodium hydroxide which passes out of the central chamber 3 as waste stream 86.

Anions present in product stream 81 such as fluoride, chloride, nitrate, phosphate and sulfate exit the ion depletion chamber 2 as the corresponding acid i.e. hydrofluoric acid, hydrochloric acid, nitric acid, phosphoric acid and sulfuric acid. The product stream 81 flows directly to the conductivity detector cell. During this process, there is a continuous flow of water from anode feed stream 18a, cathode feed stream 18b, and central chamber feed stream 18c. In the anode chamber 8, the water stream 18a provides water for electrolysis producing hydronium and oxygen gas, $O_2$ and anode waste stream 85. In the cathode chamber 10 the water stream 18b provides water for electrolysis producing hydroxide and hydrogen gas, $H_2$ and cathode waste stream 84.

In FIGS. 12 and 13, the dimensions of the homogeneous ion depletion chamber in which the eluent is flowing (homogenous anion depletion chamber 1 for FIG. 12 and homogeneous cation depletion chamber 2 for FIG. 13) may be reduced so that the volume of the ion depletion chamber is sufficiently small so as to minimize band broadening effects which would be detrimental to the chromatographic separation. The ability to suppress or neutralize the eluent is dependent on the volume of the homogeneous ion depletion chamber (homogenous anion depletion chamber 1 for FIG. 12 and homogeneous cation depletion chamber 2 for FIG. 13) and the applied voltage and current. Depending on the types of eluents used for the analysis of anions and cations, it may be desirable to optimize the volume of the individual homogeneous anion and homogeneous cation depletion chambers. By adjusting the volumes of the homogeneous ion depletion chambers, it is possible to optimize suppression capacity in each chamber.

FIG. 14 shows a method for the simultaneous suppression of anions and cations for ion chromatography. The processes described for FIGS. 12 and 13 occur simultaneously in the configuration shown in FIG. 14. Since a single power supply is used, the limiting applied current is determined by the highest eluent concentration used or by the homogeneous ion depletion chamber requiring the highest current for complete suppression. Note that in this configuration, the central heterogeneous anion and cation concentration chamber waste stream 96 results from combing the acid eluent, hydrochloric acid, and base eluent, sodium hydroxide, forming a salt waste product, sodium chloride.

The method of ion suppression of the present invention solves the problems in the background art that occur when common mineral acids, such as hydrochloric acid or nitric acid are used. This method of ion suppression disclosed here, using the CEDI device described above, allows for cation suppression in the presence of chloride, nitrate, and other electrochemically active anions, without the damage to the ion suppressor.

DATA FOR EXAMPLE EMBODIMENTS

Example 1

This is an example of the method described above for the neutralization of an acid using the specialized CEDI apparatus described above.

A specialized CEDI apparatus as shown in FIG. 3 was constructed using machined high density polyethylene hardware to retain the electrodes, membranes and resin. The internal flow through dimensions of the homogeneous cation depletion chamber and homogeneous anion depletion chamber was 1.27 cm in diameter and 3.81 cm in length. The central heterogeneous anion and cation concentration chamber dimension was 1.27 cm (diameter) and 1.27 cm (length). Defining the homogeneous cation depletion chamber were cation exchange membranes (CMI-7000 Membranes International, Glen Rock, N.J.). Disposed between the cation exchange membranes was hydronium form Dowex 50W×4 cation exchange resin (200 mesh). Defining the homogeneous anion depletion chamber were anion exchange membranes (AMI-7001 Membranes International, Glen Rock, N.J.). Disposed between the anion membranes was hydroxide form Dowex 1×4 anion exchange resin (200 mesh). The mixed bed resin in the central heterogeneous anion and cation concentration chamber consisted of Dowex 50W×4 and Dowex 1×4 in the hydronium and hydroxide forms, respectively. Platinum gauze electrodes (Unique Wire Weaving Inc, Hillside, N.J.) or similar were used.

A Dionex GP50 chromatography pump was used to deliver 0.05 M hydrochloric acid to the anion depletion chamber at a flow rate of 1.0 mL/min as shown in FIG. 9. Deionized water was pumped into the homogeneous cation depletion chamber then into the heterogeneous anion and cation concentration chamber at a flow rate of 2.0 mL/min. Deionized water was also pumped into the anode and cathode chambers at a flow rate of 2.0 mL. A Barnant dual channel peristaltic pump was used to deliver the deionized water. A Dionex CD20 conductivity detector with a flow through conductivity cell was used for the conductivity measurements. From the Dionex GP50 pump, the 0.05M hydrochloric acid was directed into the homogeneous anion depletion chamber and out to the conductivity cell and then to waste.

A VWR AccuPower 4000 laboratory power supply was used to power the device as shown in FIG. 9. The power supply was operated at 100 mA in the constant current mode with an initial voltage of 53V. Gas evolution was observed immediately from the anode and cathode chambers. The initial background conductivity from the anion depletion chamber was 3.2 µS/cm. After one hour, the background had decreased to 0.91 µS/cm and the conductivity was 56 V. After eight hours, the conductivity was 0.52 µS/cm and the voltage 55V. The EDI device was allowed to run uninterrupted for 24 hours and the product water conductivity was 0.42 µS/cm. After an additional 48 hours, the background conductivity was 0.44 µS/cm and the voltage 55V demonstrating the ability to neutralize dilute hydrochloric acid by the method disclosed herein using the specialized CEDI apparatus described above.

Example 2

This is an example of the method described above for the neutralization of a base using the specialized CEDI apparatus described above.

A device as that described in the method of Example 1 was used as shown in FIG. 10 to neutralize 0.05M sodium hydroxide. The 0.05 M sodium hydroxide was pumped at 1.0 mL/min into the homogeneous cation depletion chamber using a Dionex GP50 chromatography pump. A Barnant dual channel peristaltic pump was used to pump deionized water into the homogeneous anion depletion chamber then into heterogeneous anion and cation concentration chamber and the second channel used to pump deionized water into the anode and cathode chambers at a flow rate of 2.0 mL/min. A Dionex CD20 conductivity detector with a flow through conductivity cell was used for the conductivity measurements. From the Dionex GP50 pump, the 0.05M sodium hydroxide was directed into the homogeneous cation depletion chamber and out to the conductivity cell and then to waste.

A VWR AccuPower 4000 laboratory power supply was used to power the CEDI apparatus used in the method as shown in FIG. 10. The power supply was operated at 100 mA in the constant current mode with an initial voltage of 63V. Gas evolution was observed immediately from the anode and cathode chambers. The initial background conductivity from the homogeneous cation depletion chamber was 5.4 µS/cm. After one hour, the background had decreased to 3.6 µS/cm and the conductivity was 60V. After eight hours, the conductivity was 1.6 µS/cm and the voltage 61V. The CEDI apparatus was allowed to run uninterrupted for 24 hours and the product water conductivity was 1.5 µS/cm. After an additional 48 hours, the background conductivity was 1.6 µS/cm and the voltage 60V demonstrating the ability to neutralize dilute sodium hydroxide by the method disclosed herein using the specialized CEDI apparatus described above. Trace carbonate in the 0.05M sodium hydroxide resulted in the slightly elevated background conductivity of 1.6 µS/cm. If the carbonate was not present, the neutralized background conductivity would have been below 1.0 µS/cm.

Example 3

The device from the method described in Example 1 was used as a cation suppressor for the analysis of cations by Ion Chromatography using the cation suppression method of the present invention as shown in FIG. 12.

Figure 15:
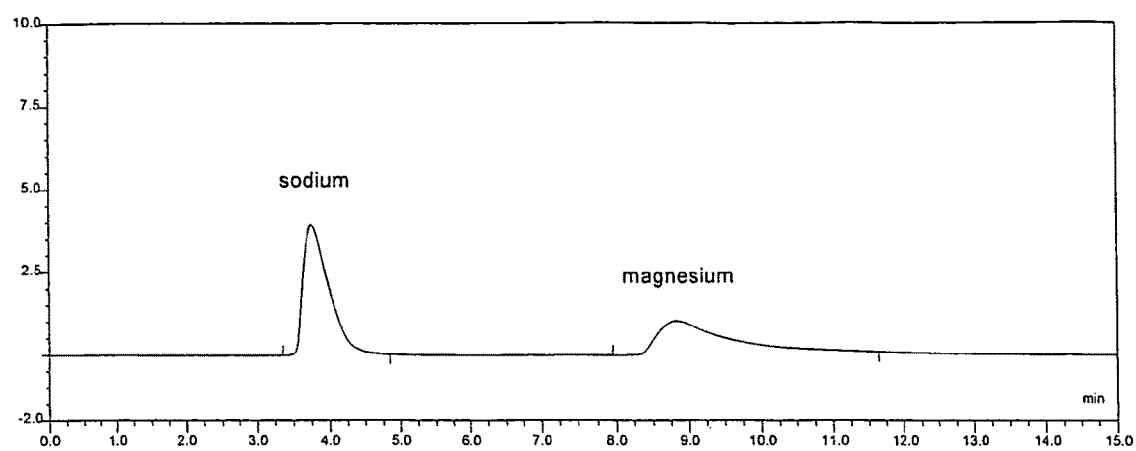
FIG. 15 shows a chromatogram for sodium and magnesium from Example 3

A Dionex ICS 2000 ion chromatograph was used with a cation exchange column using an eluent consisting of 0.010M hydrochloric acid at 1.0 mL/min. The eluent from the cation exchange column was directed to the homogeneous anion depletion chamber. A Barnant dual channel peristaltic pump was used to pump deionized water into the homogeneous cation depletion chamber then into the heterogeneous anion and cation concentration chamber and the second channel used to pump deionized water into the anode and cathode chambers at a flow rate of 2.0 mL/min. A VWR AccuPower 4000 laboratory power supply was used to power the device at a constant current of 33 mA. The background conductivity was 0.43 µS/cm. A standard containing 10 mg/L of sodium and 10 mg/L of magnesium was injected (50 µL) and the chromatogram shown in FIG. 15 was obtained.

Example 4

The device from the method described in Example 1 was used as an anion suppressor for the analysis of anions by Ion Chromatography using the anion suppression method of the present invention as shown in FIG. 13.

Figure 16:
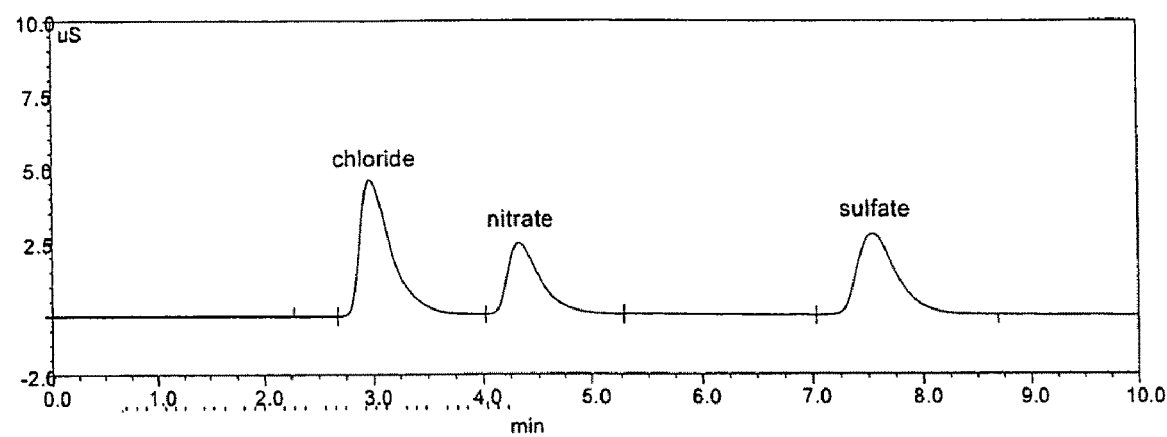
FIG. 16 shows a chromatogram for chloride, nitrate, and sulfate from Example 4.

A Dionex ICS 2000 ion chromatograph was used with an anion exchange column with an eluent consisting of 0.010M sodium hydroxide at 1.0 mL/min. The eluent from the anion exchange column was directed to the homogeneous cation depletion chamber. A Barnant dual channel peristaltic pump was used to pump deionized water into the homogeneous anion depletion chamber then into the heterogeneous anion and cation concentration chamber at 2.0 mL/min. The second channel was used to pump deionized water into the anode and cathode chambers at a flow rate of 2.0 mL/min. A VWR AccuPower 4000 laboratory power supply was used to power the device at a constant current of 33 mA. The background conductivity was 0.54 µS/cm. A standard containing 10 mg/L chloride, 10 mg/L nitrate and 10 mg/L sulfate (50 µL) was injected (50 µL) and the chromatogram shown in FIG. 16 was obtained.

Figure 17:
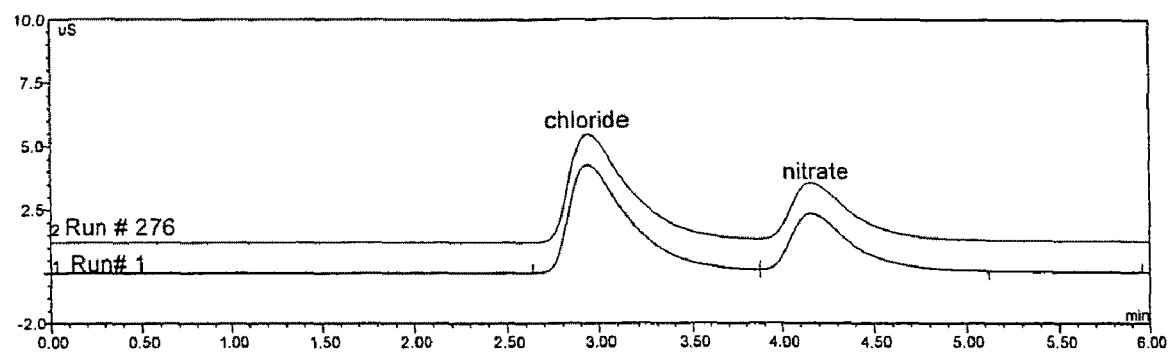
FIG. 17 shows chromatograms for chloride and nitrate from Example 4.

Next, a standard containing 10 mg/L chloride and 10 mg/L nitrate was used to demonstrate long term ion suppression capability as shown in FIG. 17. The example shows the first run and last run of a series of 276 consecutive injections of the standard. The background conductivity remained between 0.5 and 0.6 µS/cm during the 28 hours of operation. Thus, the method of ion suppression of the present invention disclosed herein allows for consistent results while using a specialized CEDI apparatus described above, that does not require periodic maintenance for the regeneration of the ion exchange materials.

Example 5

The device from the method described in Example 1 was used for the ion chromatography method described above. The method uses the specialized CEDI apparatus as a combination anion suppressor and eluent purifier for the removal of trace anions from the sodium hydroxide eluent as shown in FIG. 18.

To demonstrate the efficiency of trace anion removal from the sodium hydroxide, the 0.010M sodium hydroxide was spiked with 0.0005 M sodium carbonate, 100. A Dionex ICS 2000 ion chromatograph was used with an anion exchange column using the sodium carbonate spiked 0.010M sodium hydroxide at 1.0 mL/min. In the first experiment, a Barnant dual channel peristaltic pump was used to pump deionized water into the homogeneous anion depletion chamber then into heterogeneous anion and cation concentration chamber and the second channel used to pump deionized water into the anode and cathode chambers at a flow rate of 2.0 mL/min. A VWR AccuPower 4000 laboratory power supply was used to power the device at a constant current of 33 mA. A standard containing 10 mg/L chloride, 10 mg/L nitrate and 10 mg/L sulfate was injected (50 µL).

In the first experiment, the eluent was not directed through the anion depletion chamber. As in Example 4 the eluent, was directed from the anion exchange column to the homogeneous cation depletion chamber. In the top chromatogram of FIG. 19, the resulting suppressed background conductivity was 6.4 µS/cm. The higher suppressed background conductivity resulted from the 0.0005 M sodium carbonate that was converted to 0.0005 M carbonic acid in the cation depletion chamber.

Figure 18:
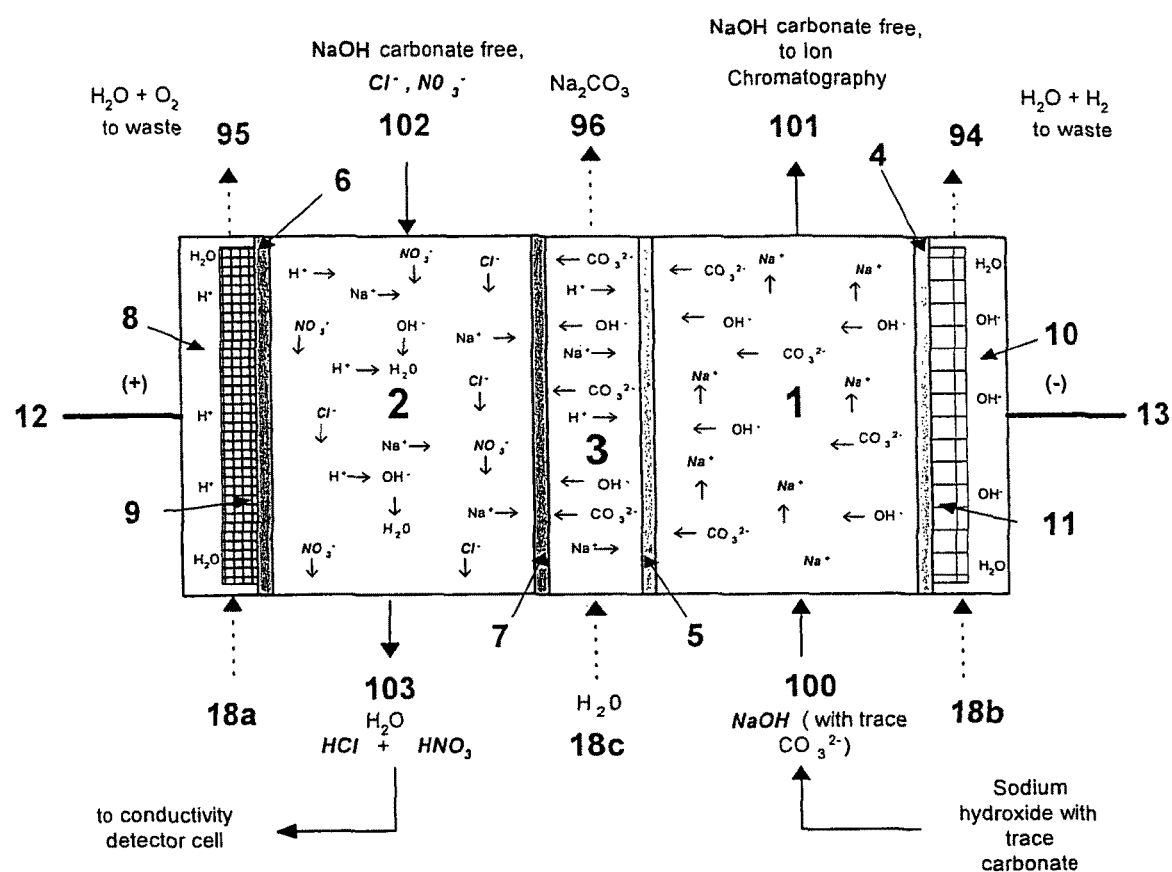
FIG. 18 shows the process fluid flow path for a method for anion suppression and trace anion removal from a base using the apparatus shown in FIG. 3 and described in Example 5.

Next, the CEDI apparatus described in the method of Example 1 was reconfigured as shown in FIG. 18 so that the carbonate spiked sodium hydroxide eluent, 100, passed through the anion depletion chamber 1 exiting as purified sodium hydroxide 101. The purified sodium hydroxide was directed to the pump of the ion chromatograph and exiting the anion exchange column as 102 and entering the cation depletion chamber 2 for ion suppression. The suppressed eluent 103 was directed to the conductivity cell. The Barnant peristaltic pump was used to deliver deionized water into the heterogeneous anion and cation depletion chambers and the electrode chambers. In the method using this configuration, trace anions such as carbonate and chloride will be removed from the eluent by the homogeneous anion depletion chamber. The lower chromatogram of FIG. 19 demonstrates the effectiveness of the trace anion removal as the suppressed background conductivity had been reduced to 0.52 µS/cm.

Example 6

In this example, 4 M KOH was used as a sample to demonstrate the method of the present invention for neutralization of a base using the specialized CEDI apparatus described above. The base is neutralized prior to analysis for trace anionic contaminants as shown in FIG. 10. The device from the method described in Example 1 was used to neutralize 50 µL of 4M KOH.

Figure 19:
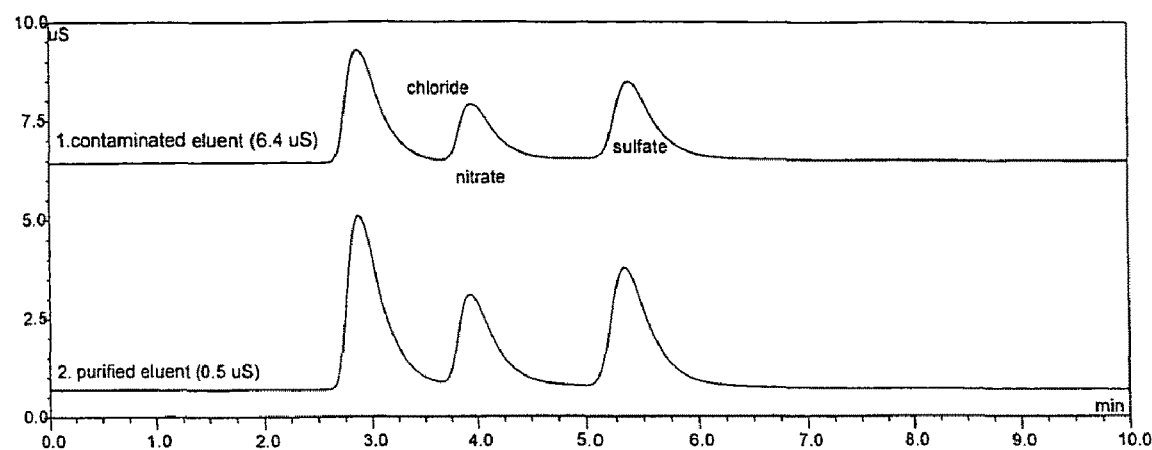
FIG. 19 shows chromatograms for chloride, nitrate, and sulfate from Example 5.
Figure 20:
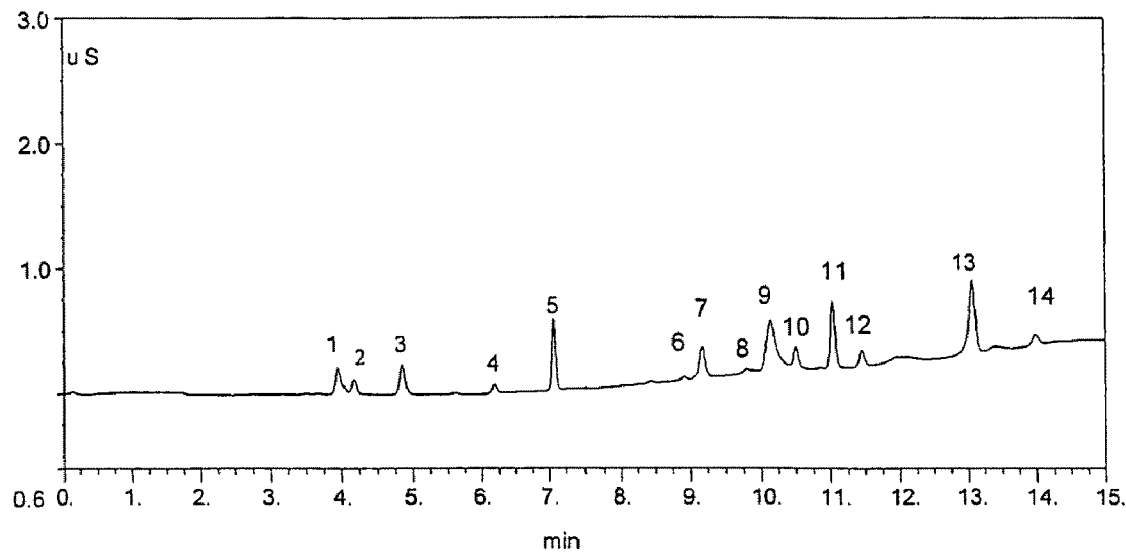
FIG. 20 shows a chromatogram for various ions from Example 6.
Figure 1:
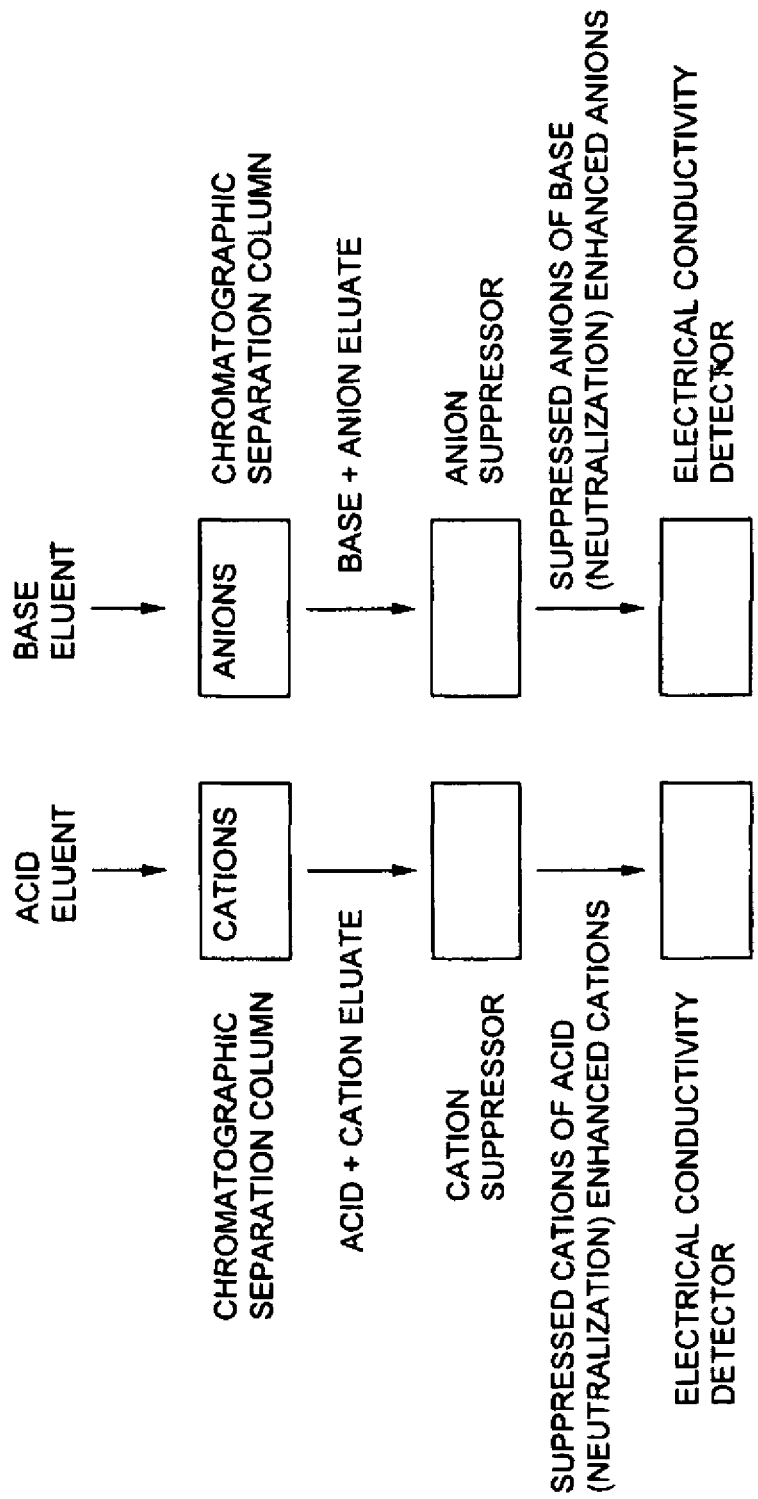
Figure 2:
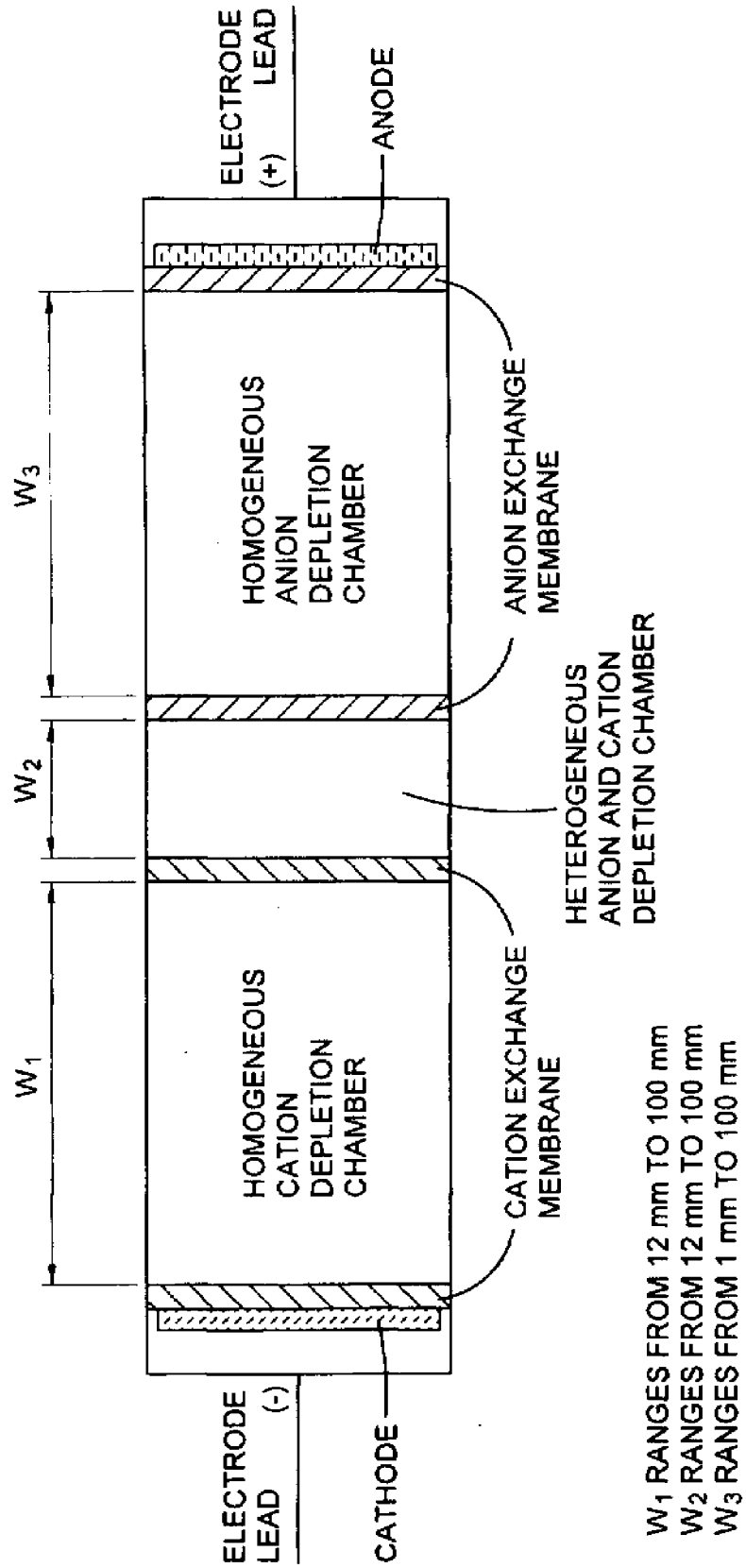
Figure 3:
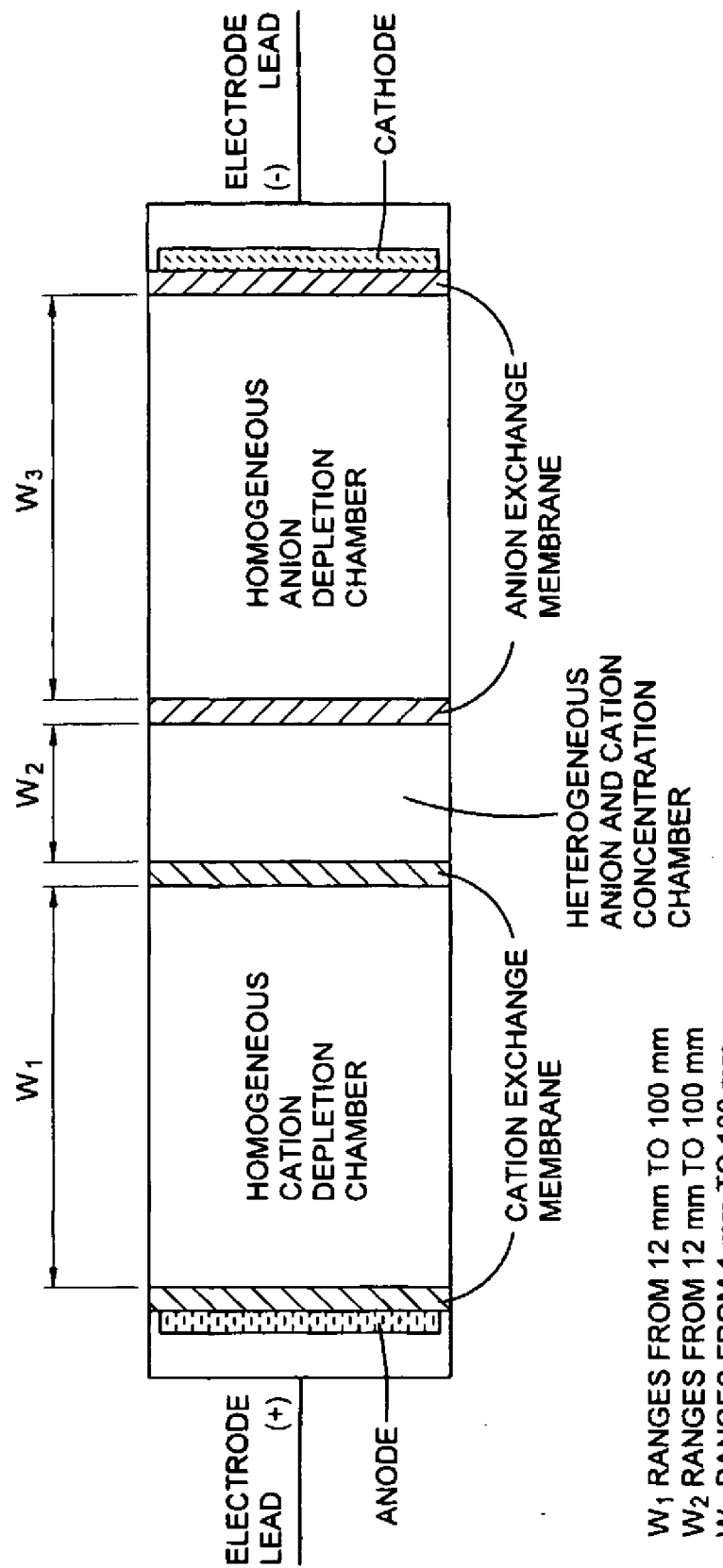
Figure 4:
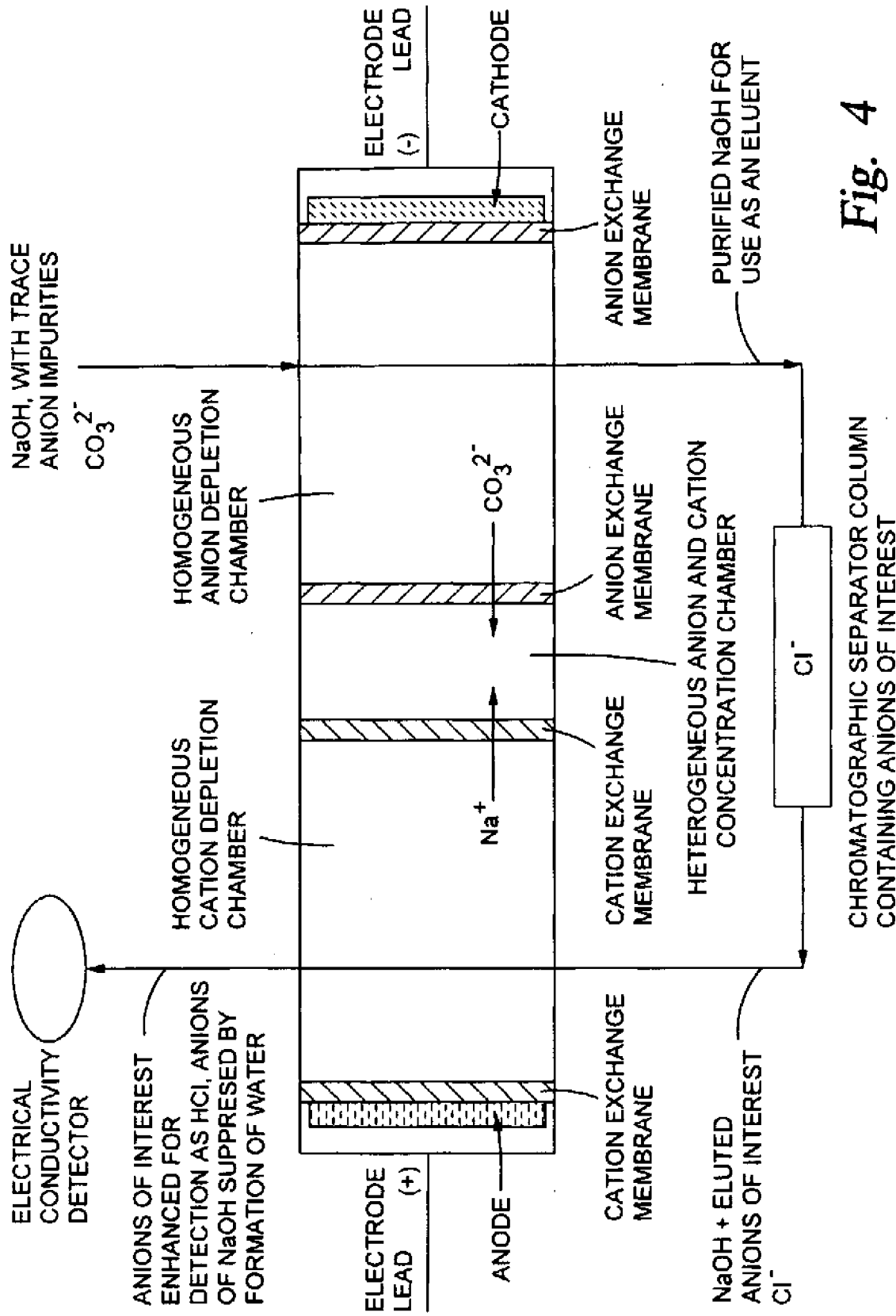
Figure 5:
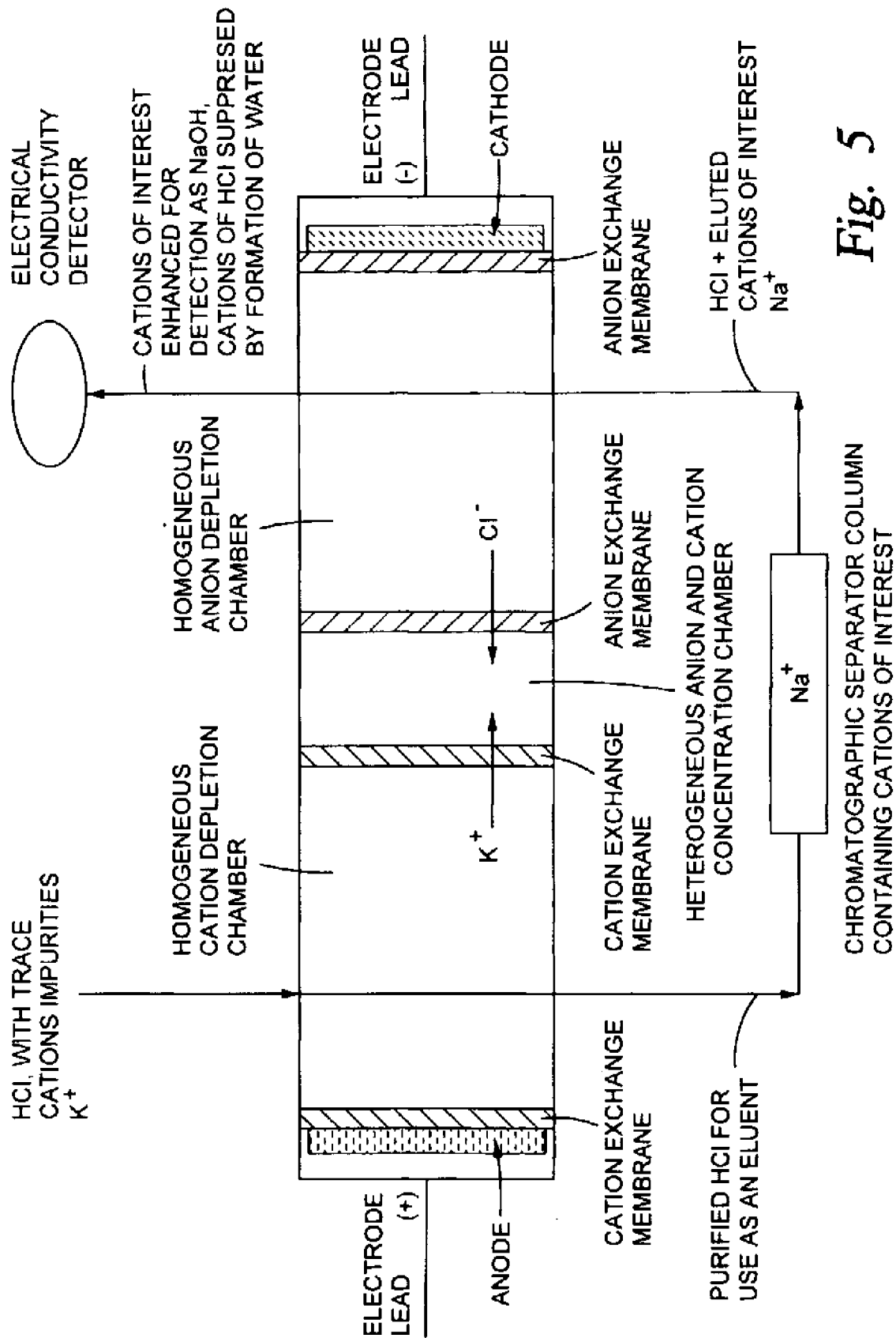
Figure 6:
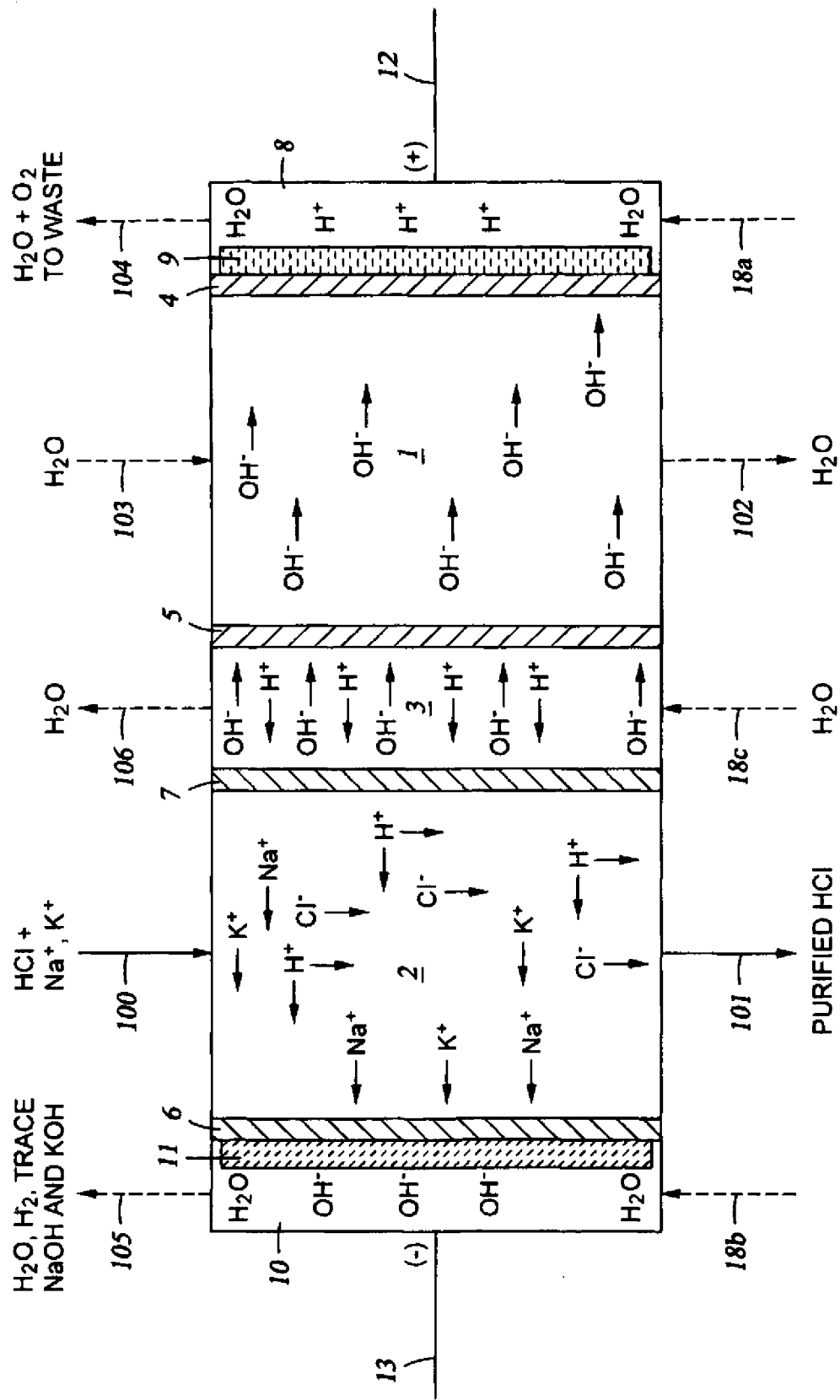
Figure 7:
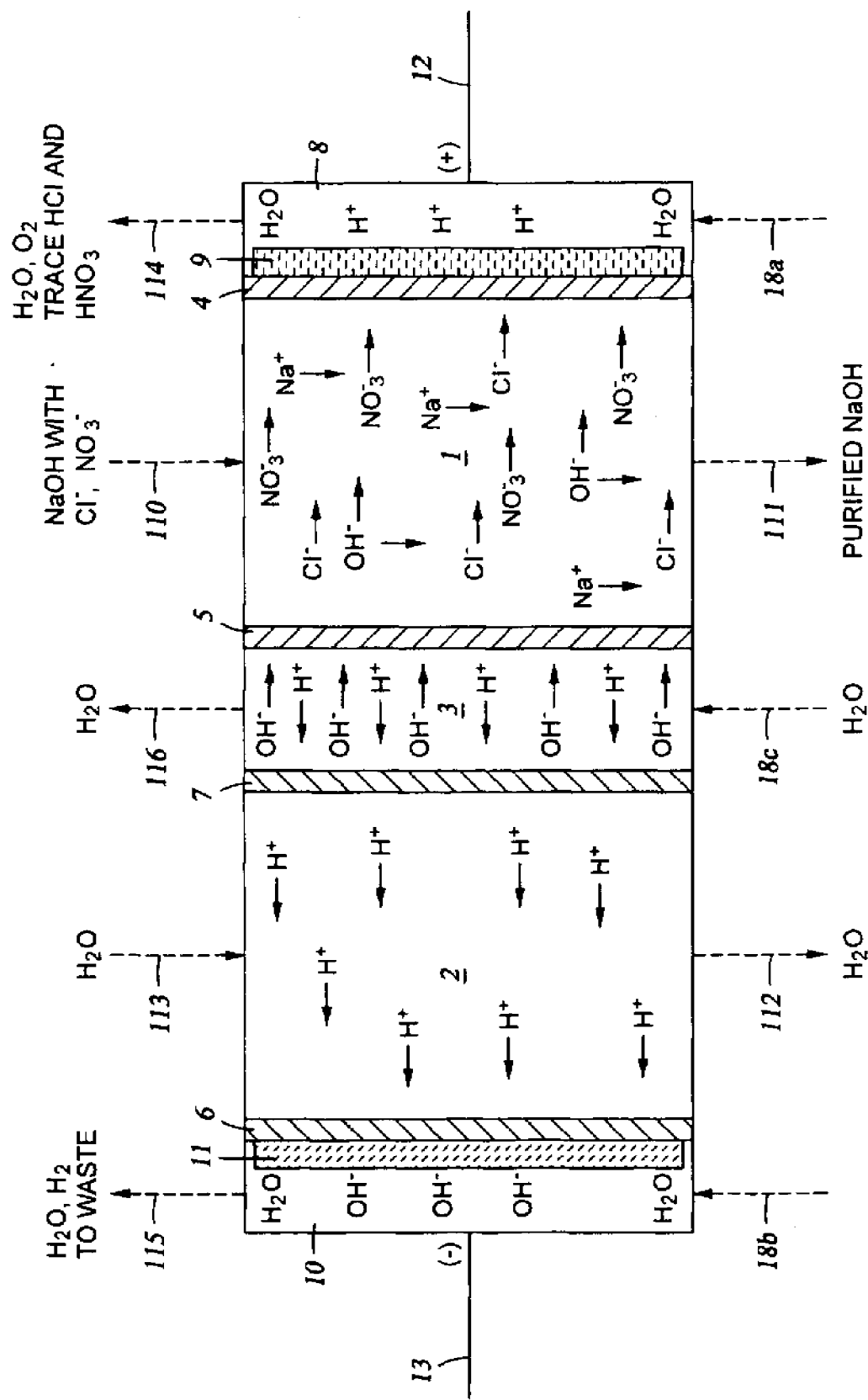
Figure 8:
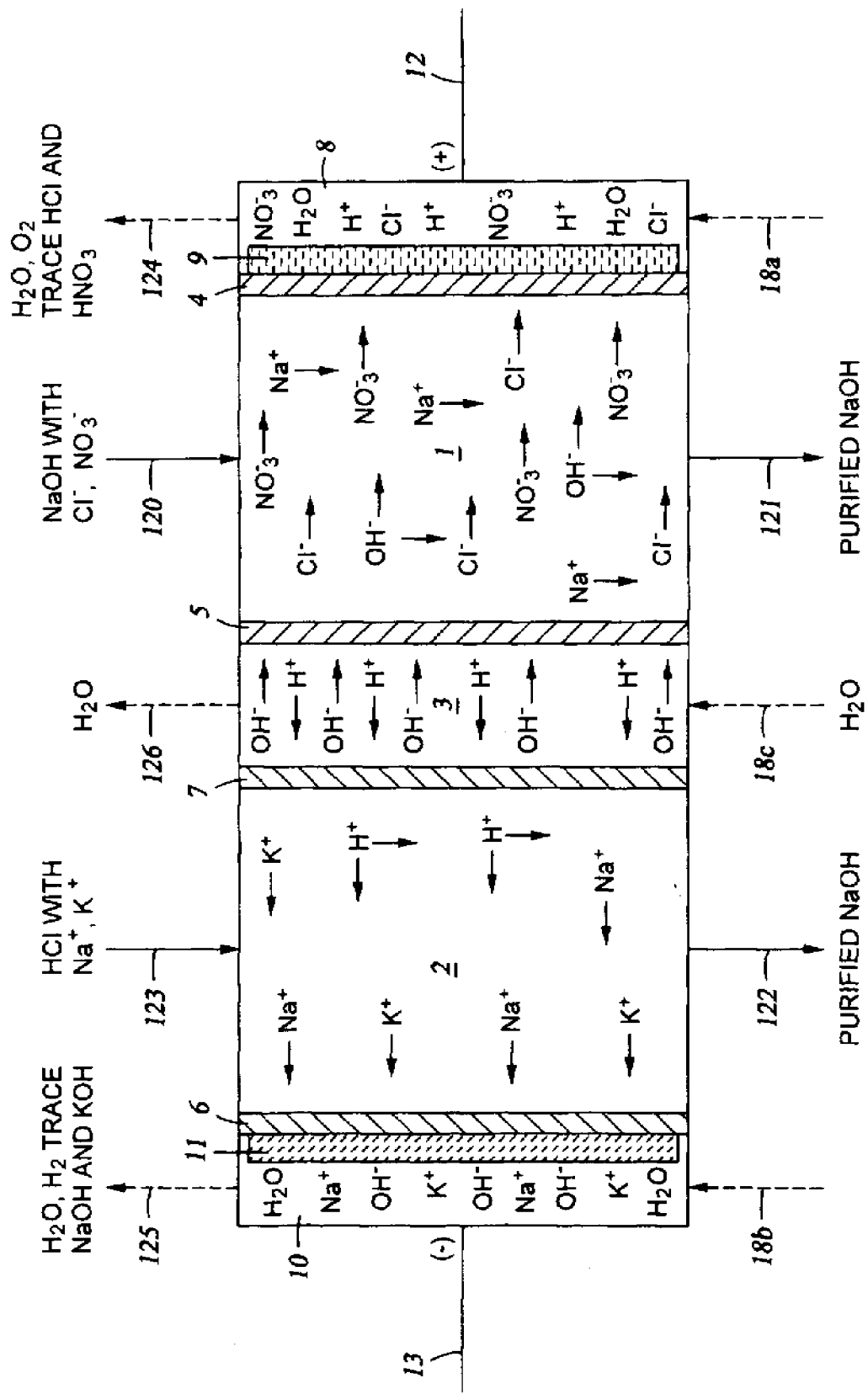
Figure 9:
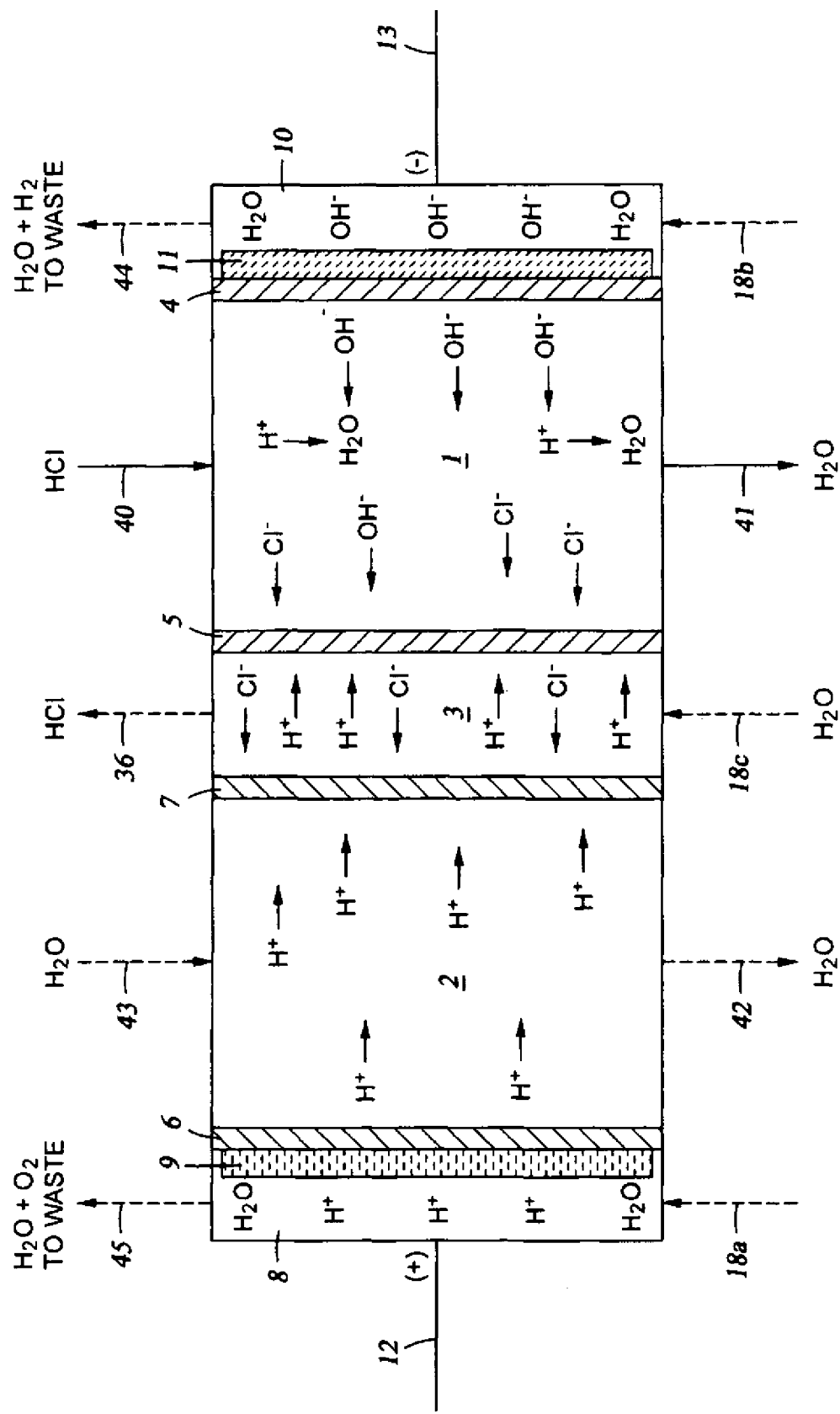
Figure 10:
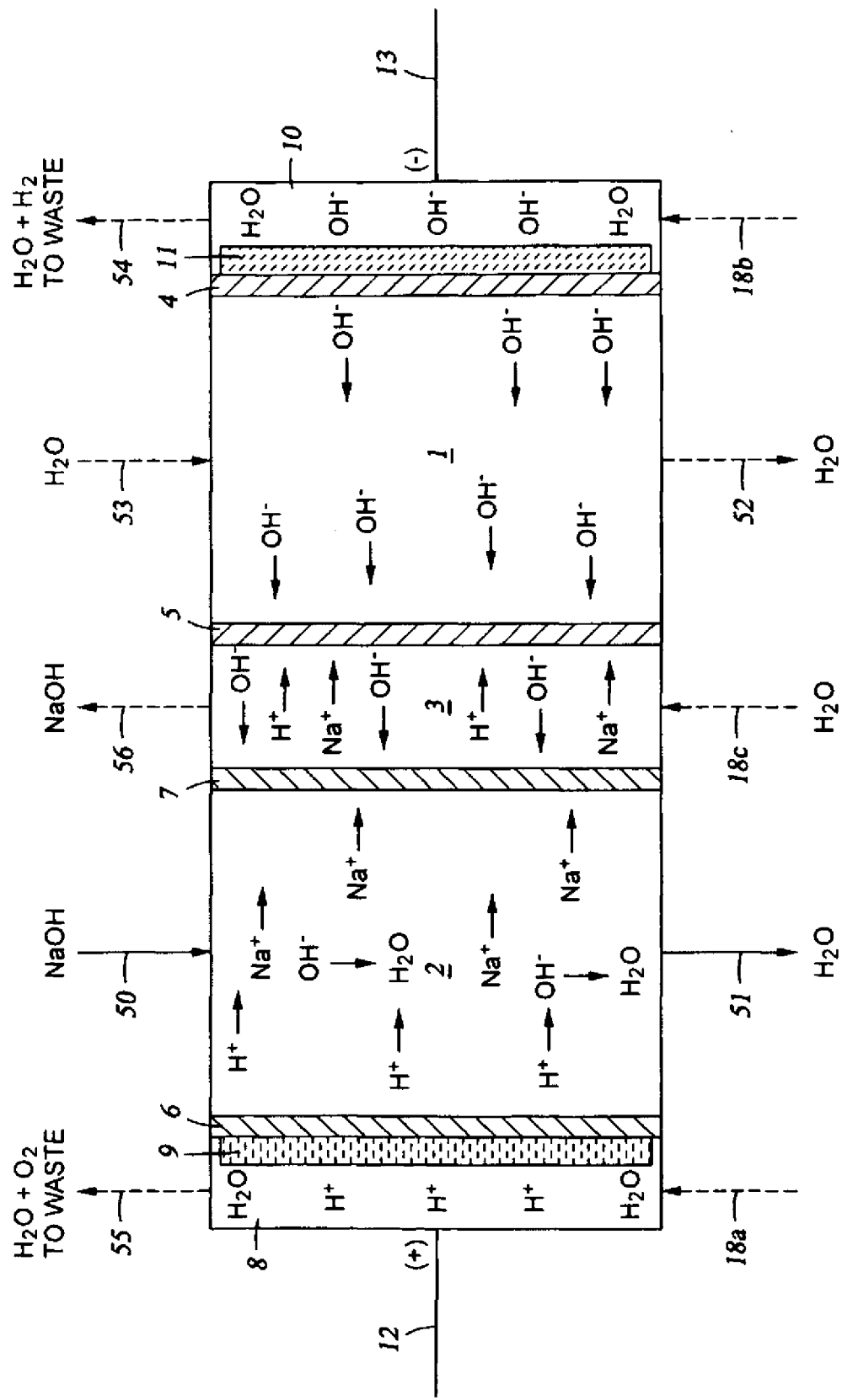
Figure 11:
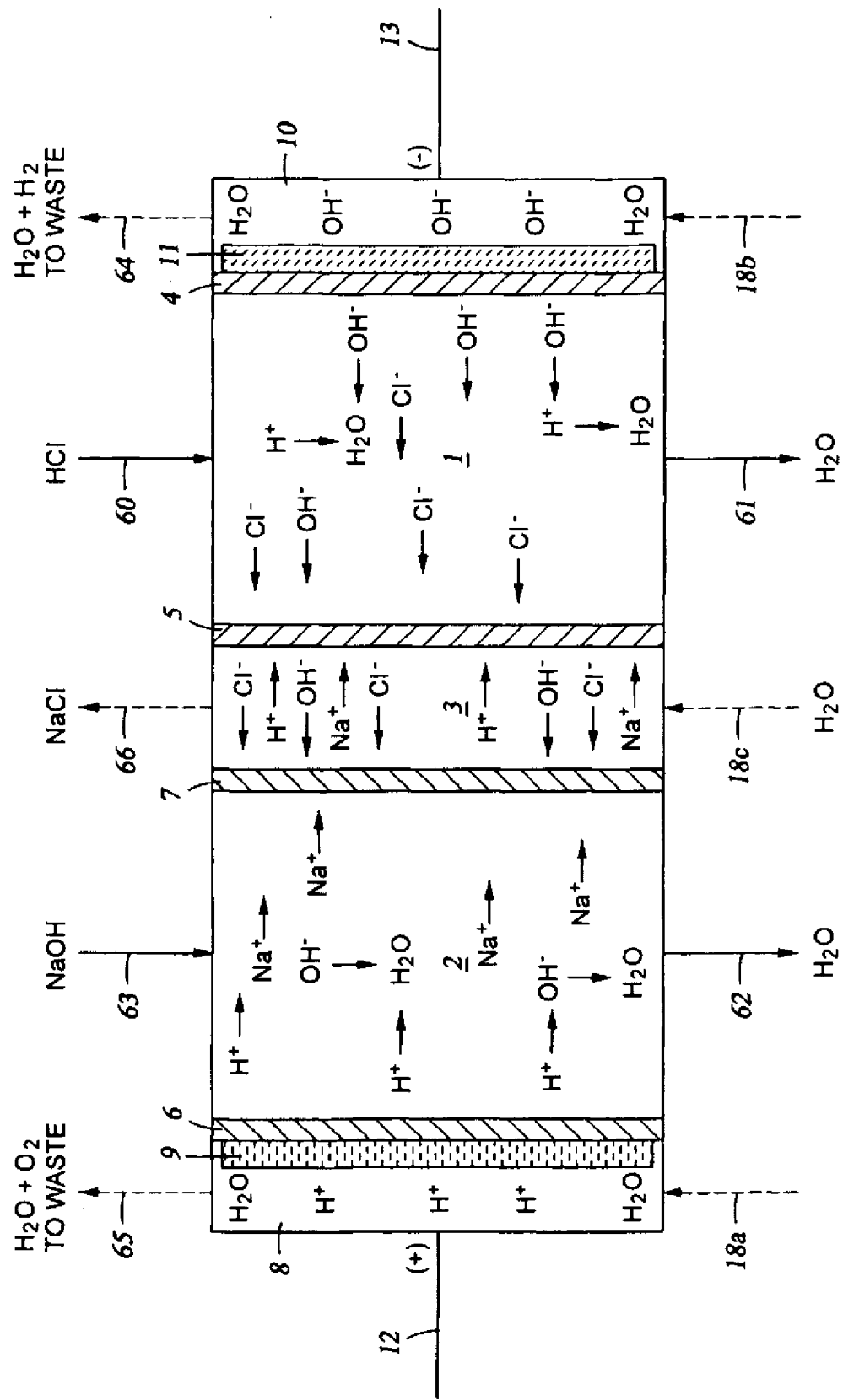
Figure 12:
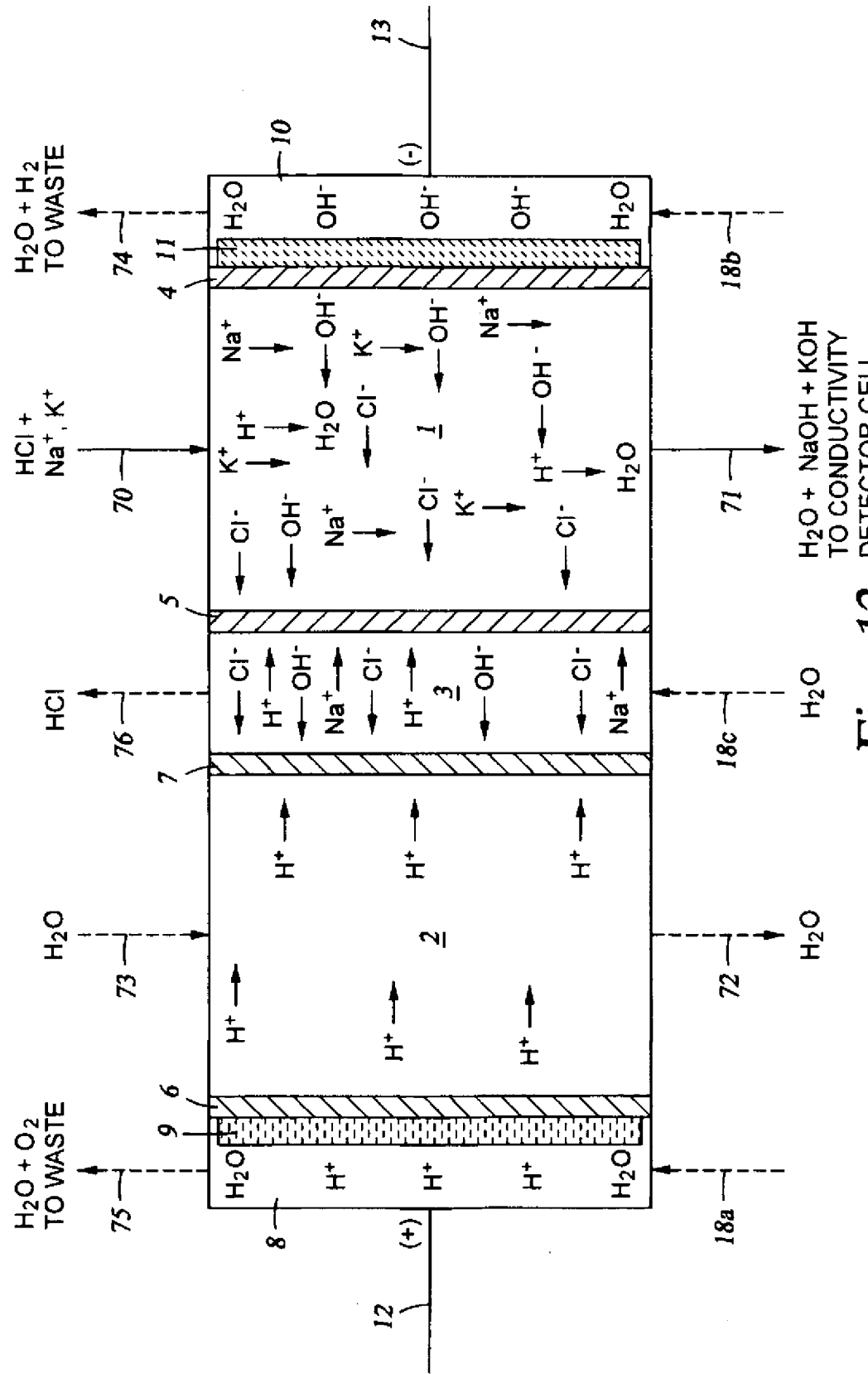
Figure 13:
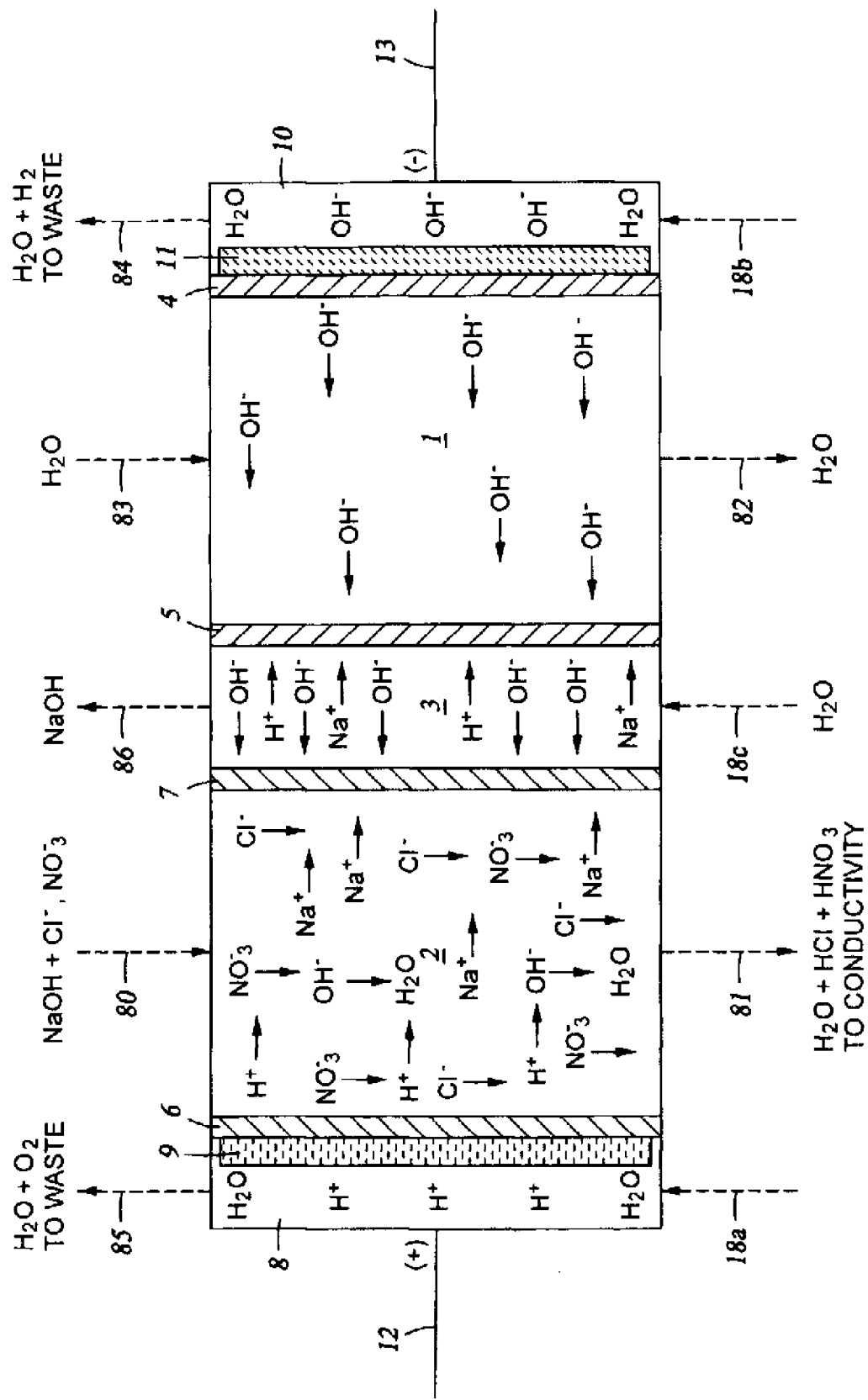
Figure 15:
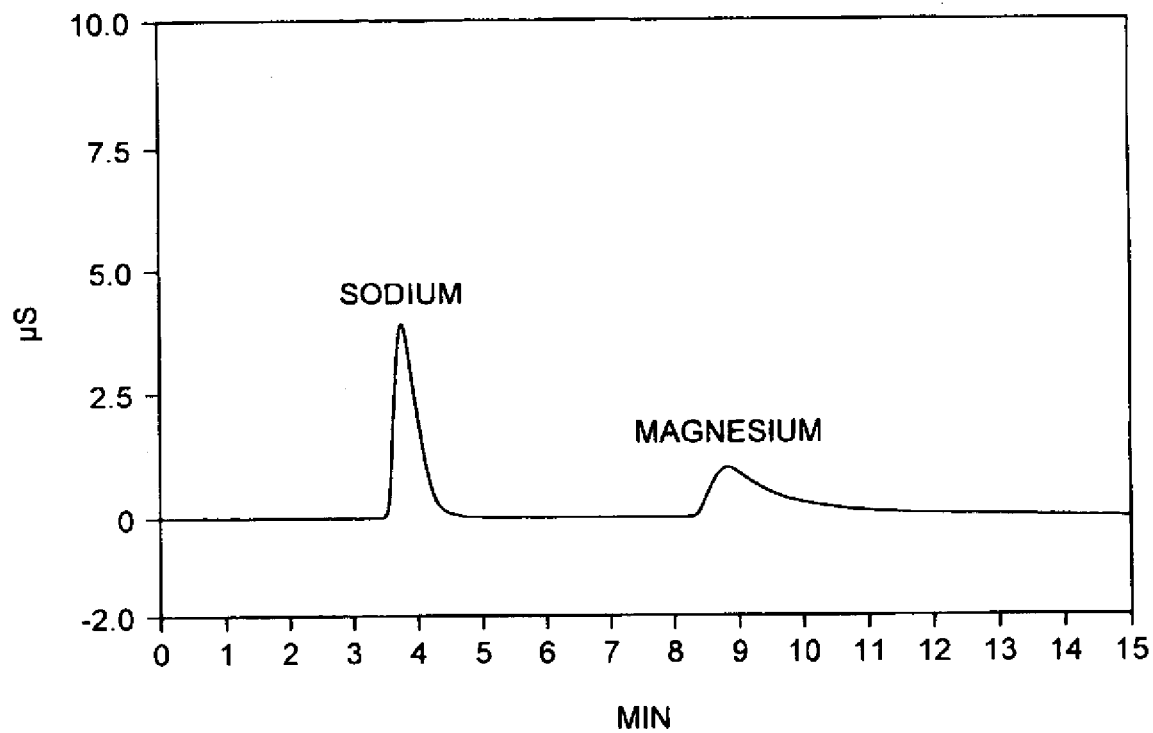
Figure 16:
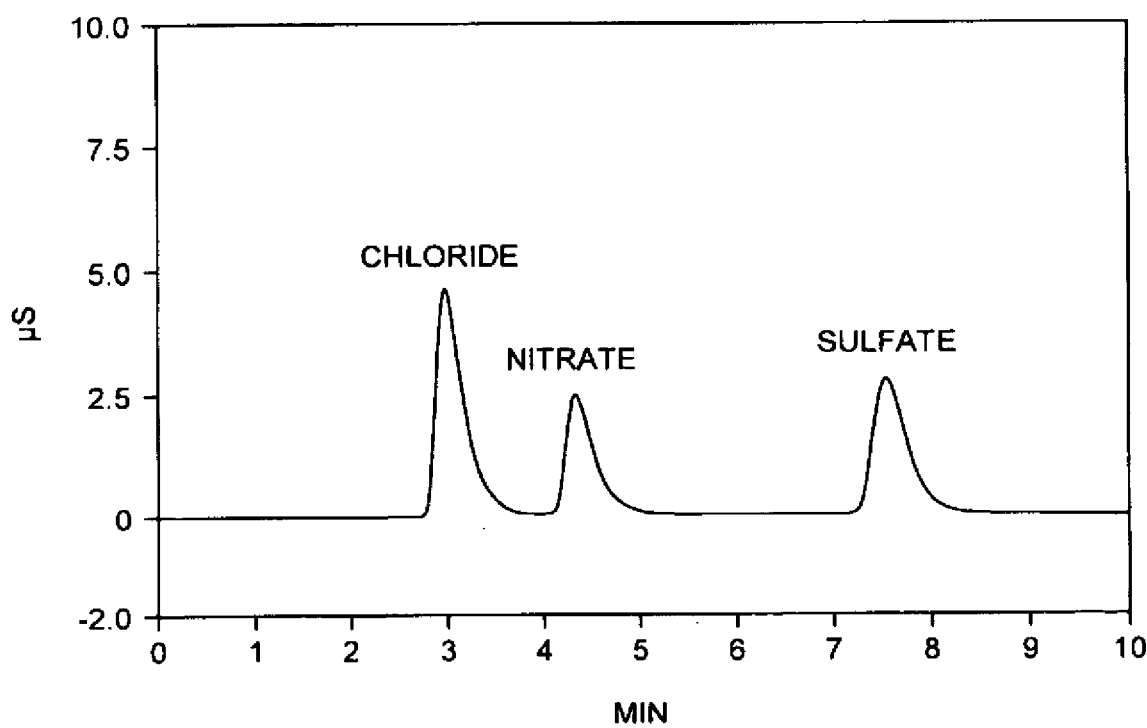
Figure 17:
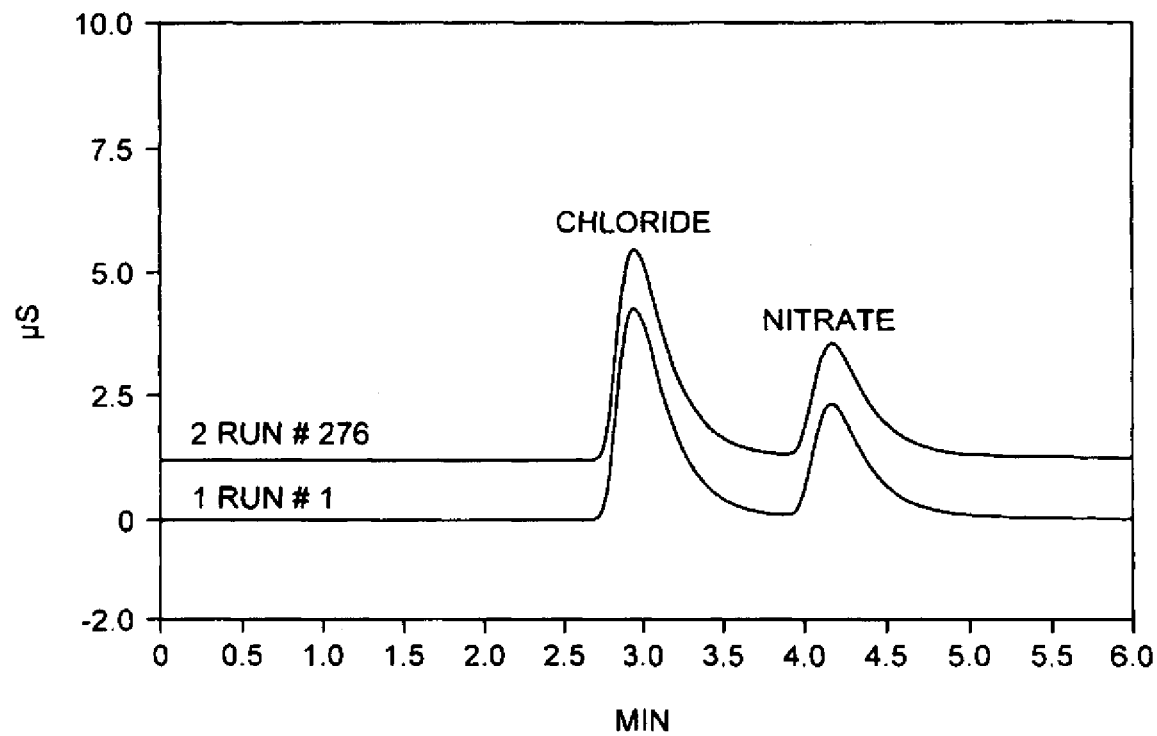
Figure 19:
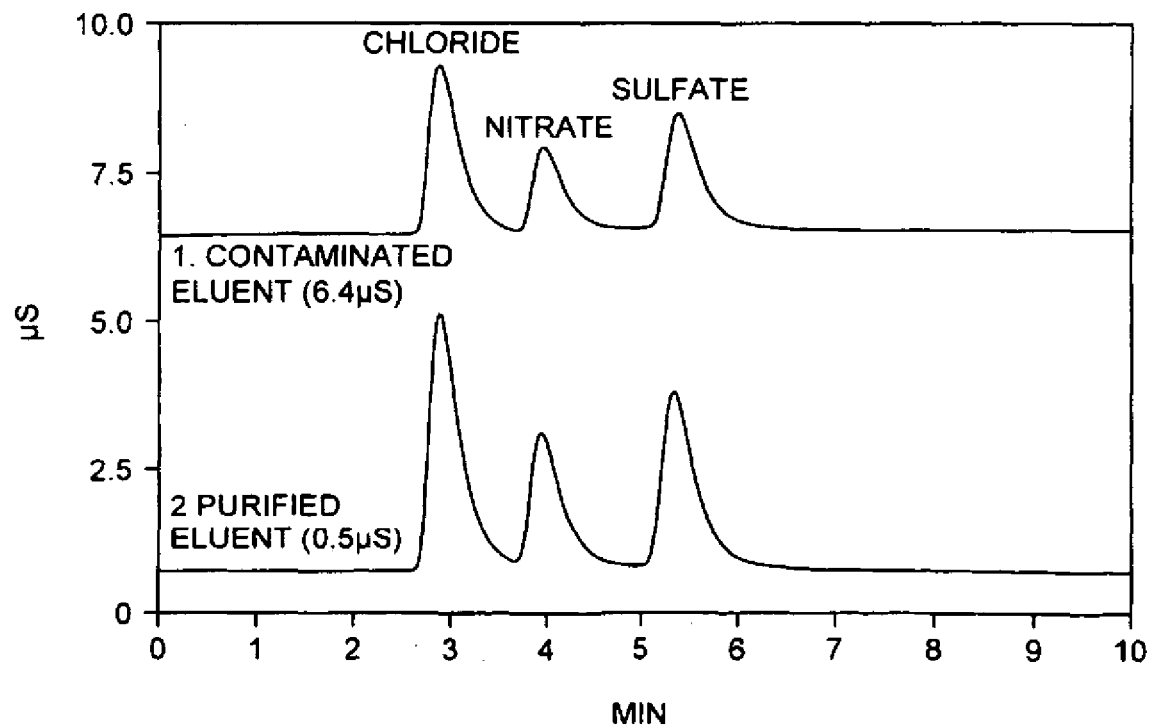
Figure 18:
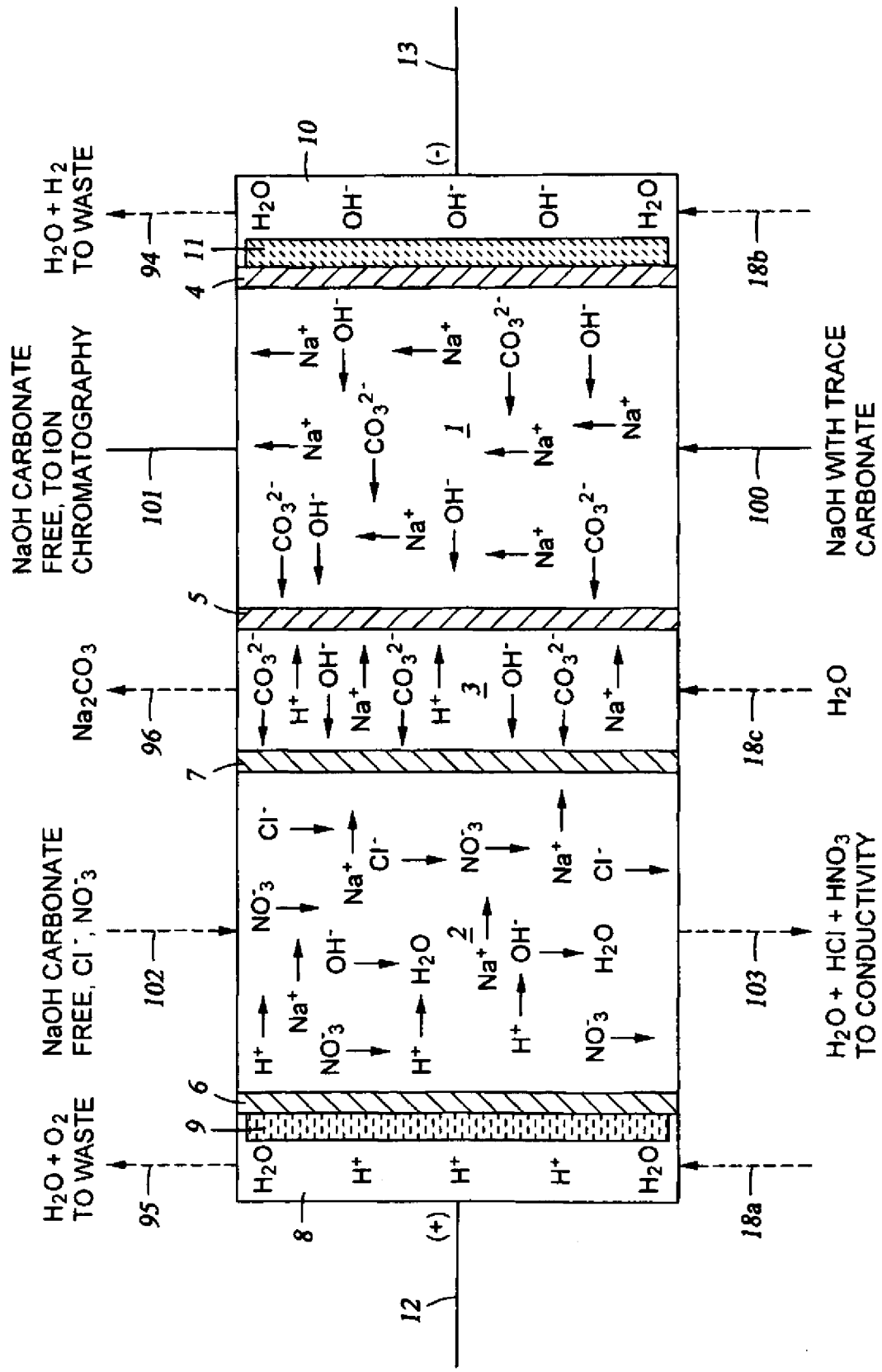
Figure 20:
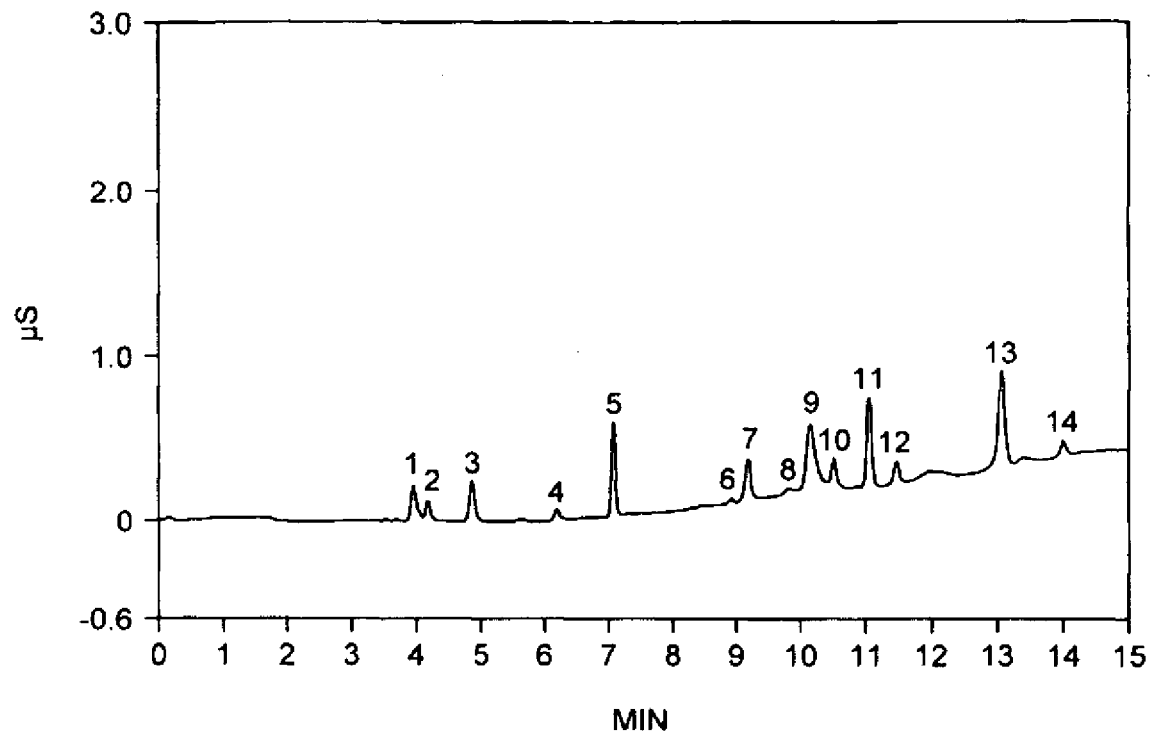

A Dionex ICS 2000 ion chromatograph was used with an anion concentrator and anion exchange column using a potassium hydroxide gradient at 0.5 mL/min. A Dionex ASRS anion suppressor was used for suppressed conductivity detection. A Barnant dual channel peristaltic pump was used to pump deionized water into the anion depletion chamber then into heterogeneous anion and cation concentration chamber and electrode chamber at 2.0 mL/min. The second channel was used to pump deionized water into the homogeneous cation depletion chamber at a flow rate of 1.0 mL/min. A VWR AccuPower 4000 laboratory power supply was used to power the device at a constant current of 100 mA. For analysis, 50 µL of 4M KOH was injected into the deionized water being pumped into the homogeneous cation depletion chamber and then collected on the anion concentrator column which was then switched in line with the potassium hydroxide eluent and the trace anions separated by gradient ion chromatography. The potassium hydroxide is neutralized in the homogeneous cation depletion chamber and trace anions present exit the homogeneous cation depletion chamber in their acid forms and are collected on the anion concentrator and the then analyzed. The result is shown in FIG. 19.

While the invention has been described in detail above with reference to several embodiments, various modifications within the scope and spirit of the invention will be apparent to those of working skill in this technological field. Accordingly, the scope of the invention should be measured by the appended claims.

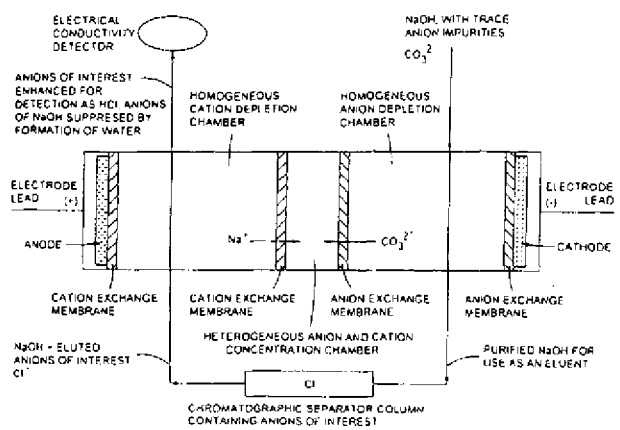

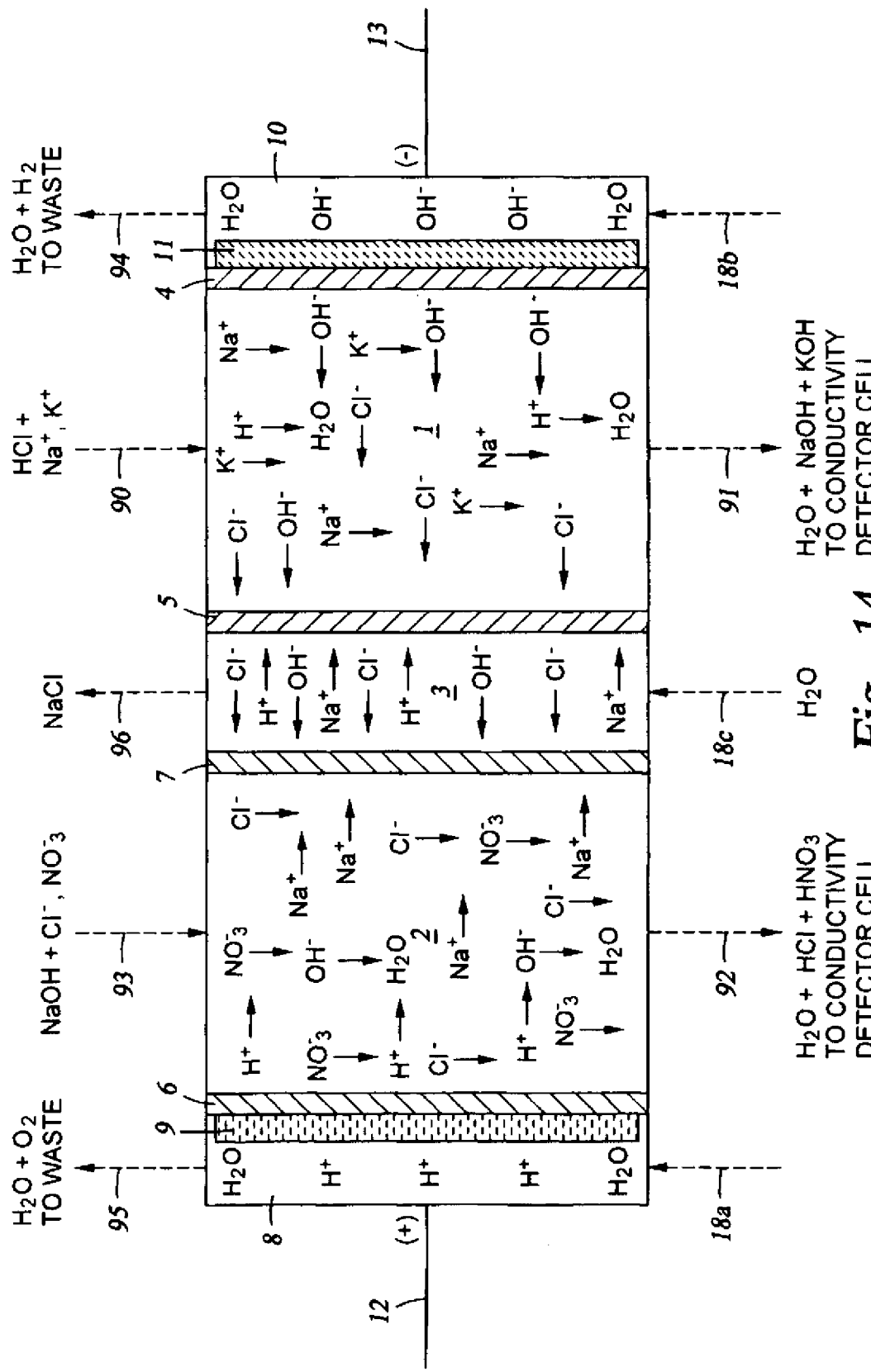

I claim:

1. A method of simultaneous anion suppression and cation suppression, using a continuous electrolytic ion exchange device, comprising:
    (a) flowing a basic solution containing an anion sample of interest through a homogeneous cation depletion chamber of said continuous electrolytic ion exchange device to suppress said basic solution by way of cation exchange occurring on cation exchange material in said homogeneous cation depletion chamber, wherein said cations are transferred from said homogeneous cation depletion chamber to a heterogeneous anion and cation concentration chamber of said continuous electrolytic ion exchange device; and
    (b) simultaneously flowing an acidic solution containing a cation sample of interest through a homogeneous anion deletion chamber of said continuous electrolytic ion exchange device to suppress said acid solution by way of anion exchange occurring on anion exchange material in said homogeneous anion depletion chamber, wherein said anions are transferred from said homogeneous anion depletion chamber to said heterogeneous anion and cation concentration chamber of said continuous electrolytic ion exchange device; and
        wherein said continuous electrolytic ion exchange device includes an anode chamber comprising an anode therein, a first cation membrane contiguous with said anode chamber, said homogeneous cation depletion chamber contiguous with said first cation membrane where said homogeneous cation depletion chamber includes said cation exchange materials therein, a second cation membrane contiguous with said cation depletion chamber, said central concentration chamber contiguous with said second cation membrane, said central concentration chamber including therein anion or cation or a mixture of anion and cation exchange materials, a first anion membrane contiguous with said central concentrate chamber, said anion depletion chamber contiguous to said first anion membrane, the anion depletion chamber including said anion exchange materials, a second anion membrane contiguous with said anion depletion chamber, and a cathode chamber comprising a cathode therein which is contiguous with said second anion membrane, and wherein a voltage is applied to achieve ion movements within said continuous electrolytic ion exchange device.

2. A method of simultaneous anion suppression and cation suppression in accordance with claim 1, wherein said anion sample of interest is enhanced by conversion to the acid form by way of cation exchange occurring on said cation exchange material in said homogeneous cation depletion chamber of said continuous electrolytic ion exchange device.

3. A method of simultaneous anion suppression and cation suppression in accordance with claim 2, wherein said enhanced acid form of said anion sample is generated by combination with hydronium.

4. A method of simultaneous anion suppression and cation suppression in accordance with claim 3, wherein said hydronium is provided by electrolysis of water occurring in said anode chamber of said continuous electrolytic ion exchange device that is located contiguous to said homogeneous cation depletion chamber.

5. A method of simultaneous anion suppression and cation suppression in accordance with claim 1, wherein said cation sample of interest is enhanced by conversion to the base form by way of anion exchange occurring on said anion exchange material in said homogeneous anion depletion chamber of said continuous electrolytic ion exchange device.

6. A method of simultaneous anion suppression and cation suppression in accordance with claim 5, wherein said enhanced base form of said cation sample is generated by combination with hydroxide.

7. A method of simultaneous anion suppression and cation suppression in accordance with claim 6, wherein said hydroxide is provided by electrolysis of water occurring in said cathode chamber of said continuous electrolytic ion exchange device that is located contiguous to said homogeneous anion depletion chamber.

8. A method of simultaneous anion and cation suppression in accordance with claim 1, wherein said basic solution containing said anion sample of interest flows into said homogeneous cation depletion chamber from a first chromatographic separation column, and said acidic solution containing said cation sample of interest flows into said homogeneous anion depletion chamber from a second chromatographic separation column.

* * * * *

UNITED STATES PATENT AND TRADEMARK OFFICE
CERTIFICATE OF CORRECTION

PATENT NO. : 8,129,194 B2
APPLICATION NO. : 12/930758
DATED : March 6, 2012
INVENTOR(S) : John M. Riviello It is certified that error appears in the above-identified patent and that said Letters Patent is hereby corrected as shown below:

The title page showing the illustrative figure should be deleted to be replaced with the attached title page.

In the drawings, Figs. 1-18 should be replaced with the corrected Figs. 1-18 as shown on the attached pages.

Column 1, lines 7-21 should read:

"Benefit of priority under 35 U.S.C. § 119(e) is claimed herein to U.S. Provisional Application No.: 60/671,371, filed April 14, 2005. The disclosure of the above referenced application is hereby incorporated by reference in its entirety herein. The parent application to the present divisional application, U.S. Serial No. 11,403,737, titled "Method Of Ion Chromatography Wherein A Specialized Electrodeioniziation Apparatus Is Used", filed April 12, 2006, is currently pending. A related application titled "Chambered Electrodeionization Apparatus With Uniform Current Density, And Method Of Use", U.S. Serial No. 11/403,737, which was filed on the same day as the parent application to the present divisional application and is hereby incorporated by reference in its entirety, and has gone abandoned after publication as US 2006-0231403 A1 on October 19, 2006."

Signed and Sealed this

Thirtieth Day of October, 2012

David J. Kappos
*Director of the United States Patent and Trademark Office*

CERTIFICATE OF CORRECTION (continued)

(12) United States Patent
Riviello

(10) Patent No.: US 8,129,194 B2
(45) Date of Patent: Mar. 6, 2012

(54) METHOD OF SIMULTANEOUS ANION AND CATION SUPPRESSION IN A CONTINUOUS ELECTRODEIONIZATION APPARATUS

(75) Inventor: John M. Riviello, Santa Cruz, CA (US)

(73) Assignee: Trovion Singapore Pte. Ltd., Co., Singapore (SG)

(*) Notice: Subject to any disclaimer, the term of this patent is extended or adjusted under 35 U.S.C. 154(b) by 0 days.

(21) Appl. No.: 12/930,758

(22) Filed: Jan. 14, 2011

(65) Prior Publication Data
US 2011/0114489 A1    May 19, 2011

Related U.S. Application Data

(62) Division of application No. 11/403,737, filed on Apr. 12, 2006, now Pat. No. 7,892,848.

(60) Provisional application No. 60/671,371, filed on Apr. 14, 2005.

(51) Int. Cl.
G01N 30/26    (2006.01)

(52) U.S. Cl. ...... 436/161; 73/61.55; 73/61.56; 73/61.58; 210/198.2; 210/656; 422/70

(58) Field of Classification Search ............... 436/161; 422/70; 210/656, 198.2; 73/61.52–61.58
See application file for complete search history.

(56) References Cited

U.S. PATENT DOCUMENTS

| | | | |
|---|---|---|---|
| 3,926,559 A | 12/1975 | Stevens | 23/230 R |
| 4,687,561 A | 8/1987 | Kunz | 204/182.5 |
| 5,045,204 A | 9/1991 | Dasgupta et al. | 210/635 |
| 5,248,426 A | 9/1993 | Stillian et al. | 210/635 |
| 5,352,360 A | 10/1994 | Stillian et al. | 210/198.2 |
| 5,518,622 A | 5/1996 | Stillian et al. | 210/635 |
| 5,569,365 A | 10/1996 | Rabin et al. | 204/450 |
| 5,597,481 A | 1/1997 | Stillian et al. | 210/198.2 |
| 5,633,171 A | 5/1997 | Small et al. | 436/161 |
| 5,759,405 A | 6/1998 | Anderson, Jr. et al. | 210/656 |
| 5,773,615 A | 6/1998 | Small et al. | 436/161 |
| 5,914,025 A | 6/1999 | Small | 205/789 |
| 5,935,443 A | 8/1999 | Anderson, Jr. et al. | 210/656 |
| 6,027,643 A | 2/2000 | Small et al. | 210/198.2 |
| 6,077,434 A | 6/2000 | Srinivasan et al. | 210/635 |
| 6,200,477 B1 | 3/2001 | Anderson, Jr. et al. | 210/198.2 |
| 6,235,197 B1 | 5/2001 | Anderson, Jr. et al. | 210/635 |

(Continued)

FOREIGN PATENT DOCUMENTS

EP    1048351 A2    11/2000

(Continued)

OTHER PUBLICATIONS

European Search Report of corresponding EP Application Serial No. 06740917.7, which corresponds with parent application (U.S. Appl. No. 11/403,737) to the present divisional application.

(Continued)

*Primary Examiner* — Jan Ludlow
(74) *Attorney, Agent, or Firm* — Shirley L. Church, Esq.

(57) ABSTRACT

The present invention pertains to a method of ion chromatography wherein a specialized electrodeionization (EDI) apparatus is used for simultaneous ion suppression of cations from a flowing base containing an anion sample of interest and ion suppression of anions from a flowing acid containing a cation sample of interest. The methods described herein allow for the ion suppression of samples containing chloride, nitrate, and other electrochemically active anions, as well as sodium, potassium, and other electrochemically active cations, without causing damage to the suppressor.

8 Claims, 20 Drawing Sheets